US012678517B2

(12) United States Patent　　　　(10) Patent No.:　US 12,678,517 B2
　　　Perlson et al.　　　　　　　　　　(45) Date of Patent: 　　Jul. 14, 2026

(54) MIRI26-5P FOR TREATING MOTOR NEURON DISEASES

(71) Applicant: RAMOT AT TEL-AVIV UNIVERSITY LTD., Tel Aviv (IL)

(72) Inventors: Eran Perlson, Tel-Aviv (IL); Roy Maimon, Tel-Aviv (IL); Oded Behar, Moshav Bayit Zait (IL)

(73) Assignee: RAMOT AT TEL-AVIV UNIVERSITY LTD., Tel-Aviv (IL)

( * ) Notice: Subject to any disclaimer, the term of this patent is extended or adjusted under 35 U.S.C. 154(b) by 1381 days.

(21) Appl. No.: 17/054,938

(22) PCT Filed: May 14, 2019

(86) PCT No.: PCT/IL2019/050545
§ 371 (c)(1),
(2) Date: Nov. 12, 2020

(87) PCT Pub. No.: WO2019/220435
PCT Pub. Date: Nov. 21, 2019

(65) Prior Publication Data
US 2021/0244828 A1　　Aug. 12, 2021

Related U.S. Application Data

(60) Provisional application No. 62/671,460, filed on May 15, 2018, provisional application No. 62/671,463, filed on May 15, 2018.

(51) Int. Cl.
*A61K 48/00*　　　(2006.01)
*A61K 9/00*　　　(2006.01)
*A61P 25/28*　　　(2006.01)
*C12N 15/113*　　(2010.01)

(52) U.S. Cl.
CPC ........ *A61K 48/0058* (2013.01); *A61K 9/0019* (2013.01); *A61P 25/28* (2018.01); *C12N 15/1136* (2013.01); *C12N 2310/141* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 9,006,195 B2 | 4/2015 | Baltimore | |
| 9,179,654 B2 | 11/2015 | Lagos-Quintana | |
| 2011/0196017 A1 | 8/2011 | Olson | |
| 2017/0009295 A1* | 1/2017 | Rigoutsos | C12Q 1/6886 |
| 2018/0064748 A1 | 3/2018 | Hornstein | |
| 2019/0117795 A1* | 4/2019 | Rodino-Klapac | C12N 15/86 |

FOREIGN PATENT DOCUMENTS

WO　　2019070741 A1　　4/2019

OTHER PUBLICATIONS

Saxena et al., Neuroprotection through Excitability and mTOR Required in ALS Motoneurons to Delay Disease and Extend Survival; Neuron 80, 80-96, Oct. 2, 2013.*
Skopenkova et al., Muscle-Specific Promoters for Gene Therapy vol. 13 No. 1 (48) 2021 | Acta Naturae | 47-58.*
Gunning P.Mol. ot-Skeletal and a-Cardiac Actin Genes Are Coexpressed in Adult Human Skeletal Muscle and Heart Cell. Biol. 1983. V. 3. No. 11. p. 1985-1995.*
Mercuri et al., Muscular dystrophies. The Lancet (2019), 394: 2025-2038 (Year: 2019).*
Agarwal et al., Predicting effective microRNA target sites in mammalian mRNAs. eLife (2015), 4:e05005 (Year: 2015).*
Al-Chalabi et al., Amyotrophic lateral sclerosis: moving towards a new classification system. The Lancet Neurology (2016), 15: 1182-1194 (Year: 2016).*
Tosolini et al., Motor neuron gene therapy: lessons from spinal muscular atrophy for amyotrophic lateral sclerosis. Frontiers in Molecular Neuroscience (2017), 10, Article 405 (Year: 2017).*
Trouth et al., Myasthenia gravis: a review. Autoimmune Diseases (2012), Article ID 874680; (Year: 2012).*
Kesner et al., Lambert-Eaton myasthenic syndrome. Neurol Clin. (2018), 36: 379-394 (Year: 2018).*
Breving et al., The complexities of microRNA regulation: mirandering around the rules. The International Journal of Biochemistry & Cell Biology (2010), 42: 1316-1329 (Year: 2010).*
MiRDB, https://mirdb.org/cgi-bin/search.cgi?searchType=miRNA&full=mirbase&searchBox=MIMAT0000444, [retrieved Dec. 5, 2024] (Year: 2024).*
Villain et al., miR-126-5p promotes retinal endothelial cell survival through SetD5 regulation in neurons. Development (2018), 145, dev156232 (Year: 2018).*
Maimon et al., Muscles secretion of toxic factors regulated by miR126-5P facilitate motor neuron degeneration in ALS. Journal of the Neurological Sciences (2017), 381, 816 (Year: 2017).*
Rinchetti et al., MicroRNA metabolism and dysregulation in amyotrophic lateral sclerosis. Mol Neurobiol (2018), 55: 6217-2630 (Year: 2018).*
Kovanda et al., Differential expression of microRNAs and other small RNAs in muscle tissue of patients with ALS and healthy age-matched controls. Scientific Reports (2018), 8:5609, pp. 1-15, published Apr. 4, 2018; and Supp Tables (Year: 2018).*
Pourshafie et al., MIR-298 Counteracts Mutant Androgen Receptor Toxicity in Spinal and Bulbar Muscular Atrophy. Molecular Therapy (2016), 24: 937-945 (Year: 2016).*
Addgene plasmid #24130, https://www.addgene.org/24130/, [retrieved Dec. 6, 2024] (Year: 2024).*
Casciaro et al., Involvement of miR-126 in autoimmune disorders. Clinical and Molecular Allergy (2018), 16:11, pp. 1-6 (Year: 2018).*
Strimpakos et al., Novel adeno-associated viral vector delivering the utrophin gene regulator jazz counteracts dystrophic pathology in mdx mice. Journal of Cellular Physiology (2014), 229: 1283-1291 (Year: 2014).*

(Continued)

*Primary Examiner* — Catherine Konopka
(74) *Attorney, Agent, or Firm* — Ballard Spahr LLP

(57)　　　　　ABSTRACT

The present invention relates to methods for treating motor neuron diseases and neuromuscular junction abnormalities. Particularly, the methods comprise increasing mi RNA 126-5p expression in skeletal muscle cells and/or motor neurons, and/or inhibiting mi RNA 126-5p expression in glial cells, thereby spatially up-regulating and/or down-regulating mi RNA 126-5p levels, and thus treating amyotrophic lateral sclerosis.

14 Claims, 14 Drawing Sheets

Specification includes a Sequence Listing.

(56) References Cited

OTHER PUBLICATIONS

Infusion Therapy, Healthline website (https://www.healthline.com/health/infusion-therapy, [retrieved Dec. 5, 2024]) (Year: 2024).*

LM608511.1, TPA: *Homo sapiens* microRNA hsa-mir-126 precursor, https://www.ncbi.nlm.nih.gov/nuccore/667478064, [retrieved Jul. 16, 2025 (Year: 2015).*

Ameres and Zamore, Diversifying microRNA sequence and function. Nature Reviews Molecular Cell Biology (2013), 14:475-488 (Year: 2013).*

Kim et al., MiR-126 regulates growth factor activities and vulnerability to toxic insult in neurons. Mol Neurobiol (2016), 53: 95-108 (Year: 2016).*

Birger et al., ALS-related human cortical and motor neurons survival is differentially affected by Sema3A. Cell Death and Disease (2018), 9:256 (Year: 2018).*

Di Pietro et al., (2017) Potential therapeutic targets for ALS: MIR206, MIR208b and MIR499 are modulated during disease progression in the skeletal muscle of patients. Sci Rep 7(1): 9538; 11 pages.

Emde and Hornstein (2014) miRNAs at the interface of cellular stress and disease. EMBO J 33(13): 1428-1437.

Fischer et al., (2004) Amyotrophic lateral sclerosis is a distal axonopathy: evidence in mice and man. Exp Neurol 185(2): 232-240.

Geser et al., (2011) On the development of markers for pathological TDP-43 in amyotrophic lateral sclerosis with and without dementia. Prog Neurobiol 95(4): 649-662.

Haramati et al., (2010) miRNA malfunction causes spinal motor neuron disease. Proc Natl Acad Sci U S A 107(29): 13111-13116.

Hawley et al., (2017) MotomiRs: miRNAs in Motor Neuron Function and Disease. Front Mol Neurosci 10: 127; 19 pages.

Ionescu et al., (2016) Compartmental microfluidic system for studying muscle-neuron communication and neuromuscular junction maintenance. Eur J Cell Biol 95(2): 69-88.

Lemmens et al., (2010) RNA metabolism and the pathogenesis of motor neuron diseases. Trends Neurosci 33(5): 249-258.

Maimon and Perlson (2019) Muscle secretion of toxic factors, regulated by miR126-5p, facilitates motor neuron degeneration in amyotrophic lateral sclerosis. Neural Regen Res 14(6): 969-970.

Maimon et al., (2017) Muscles secretion of toxic factors regulated by miR126-5P facilitate motor neuron degeneration in ALS. Journal of the Neurological Sciences 381(Supplement): 816.

Maimon et al., (2018) miR126-5p Downregulation Facilitates Axon Degeneration and NMJ Disruption via a Non-Cell-Autonomous Mechanism in Als. J Neurosci 38(24): 5478-5494.

Martineau et al., (2018) Dynamic neuromuscular remodeling precedes motor-unit loss in a mouse model of ALS. Elife 7: e41973; 19 pages.

Molasy et al., (2017) MicroRNAs in glaucoma and neurodegenerative diseases. J Hum Genet 62(1): 105-112.

Molofsky et al., (2014) Astrocyte-encoded positional cues maintain sensorimotor circuit integrity. Nature. Author manuscript; available in PMC Nov. 8, 2014. Published in final edited form as: Nature. May 8, 2014; 509(7499): 189-194.

Nachmany et al., (2012) Two potential biomarkers identified in mesenchymal stem cells and leukocytes of patients with sporadic amyotrophic lateral sclerosis. Dis Markers 32(4): 211-220.

Porter (1999) Protein translocation in apoptosis. Trends in Cell Biology 9(10): 394-401.

Reyes et al., (2010) Blocking the mitochondrial apoptotic pathway preserves motor neuron viability and function in a mouse model of amyotrophic lateral sclerosis. J Clin Invest 120(10): 3673-3679.

Rotem et al., (2017) ALS Along the Axons—Expression of Coding and Noncoding RNA Differs in Axons of ALS models. Sci Rep 7: 44500; 17 pages.

Saraiva et al., (2016) Traceable microRNA-124 loaded nanoparticles as a new promising therapeutic tool for Parkinson's disease. Neurogenesis (Austin) 3(1): e1256855; 8 pages.

Scotter et al., (2015) TDP-43 Proteinopathy and ALS: Insights into Disease Mechanisms and Therapeutic Targets. Neurotherapeutics 12(2): 352-363.

Wen et al., (2014) Antisense proline-arginine RAN dipeptides linked to C9ORF72-ALS/FTD form toxic nuclear aggregates that initiate in vitro and in vivo neuronal death. Neuron 84(6): 1213-1225.

Zahavi et al., (2015) A compartmentalized microfluidic neuromuscular co-culture system reveals spatial aspects of GDNF functions. J Cell Sci 128(6): 1241-1252.

Zheng et al., (2018) Altered motor axonal excitability in patients with cervical spondylotic amyotrophy. Clin Neurophysiol 129(7): 1383-1389.

Mature sequence hsa-miR-126-3p; Accession No. MIMAT0000445. Retrieved from: http://www.mirbase.org/cgi-bin/mature.pl?mature_acc=MIMAT0000445, on Jan. 27, 2021. 3 pages.

Birger et al., ALS-related human cortical and motor neurons survival is differentially affected by Sema3A, Cell Death Dis, 2018, pp. 1-9, 9(3): 256.

Casciaro et al., Involvement of miR-126 in autoimmune disorders. Clin Mol Allergy, 2018, pp. 1-6, 16:11.

Kim et al., (2016) MiR-126 Regulates Growth Factor Activities and Vulnerability to Toxic Insult in Neurons. Mol Neurobiol, 2016, pp. 95-108, 53(1).

Villain et al., miR-126-5p promotes retinal endothelial cell survival through SetD5 regulation in neurons. Development, 2018, pp. 1-15, 145(1): dev156232.

* cited by examiner

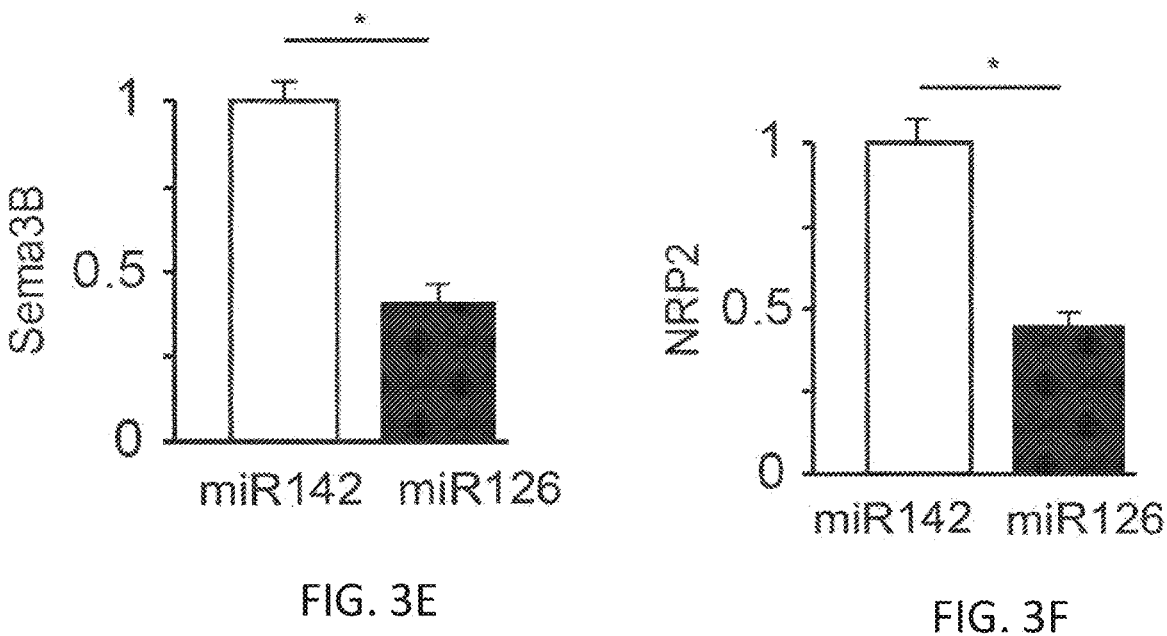
FIG. 3E
FIG. 3F
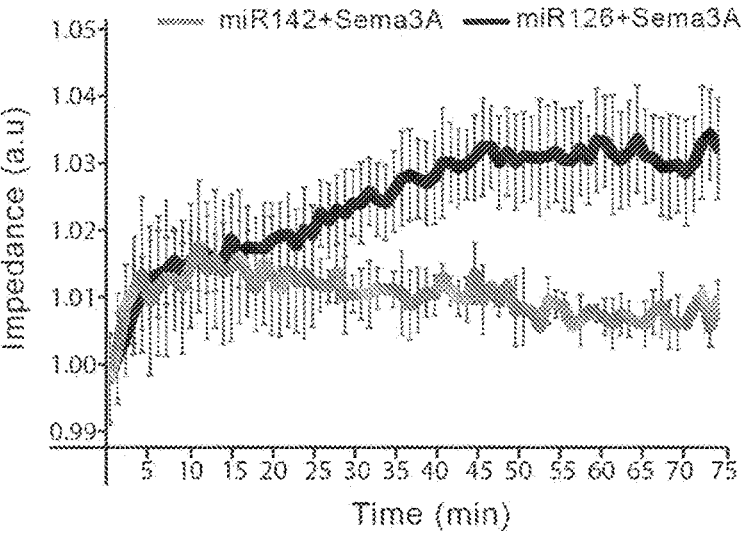
FIG. 3G

FIG. 4D
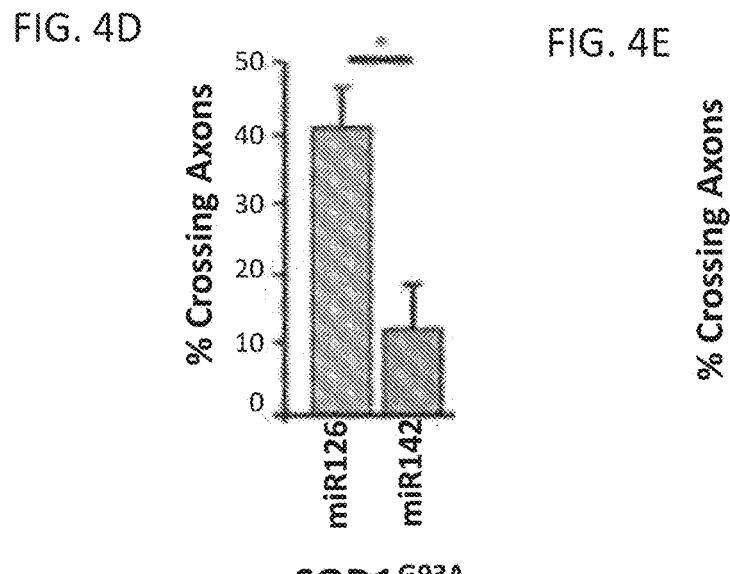
SOD1$^{G93A}$
FIG. 4E
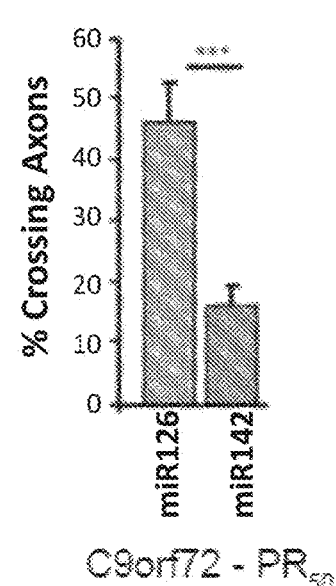
C9orf72 - PR$_{50}$
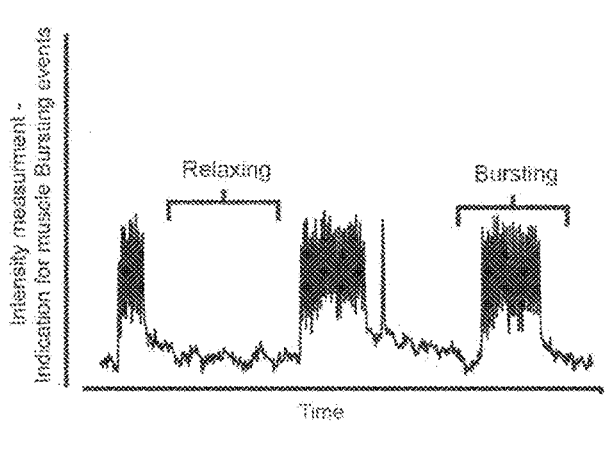
FIG. 4F
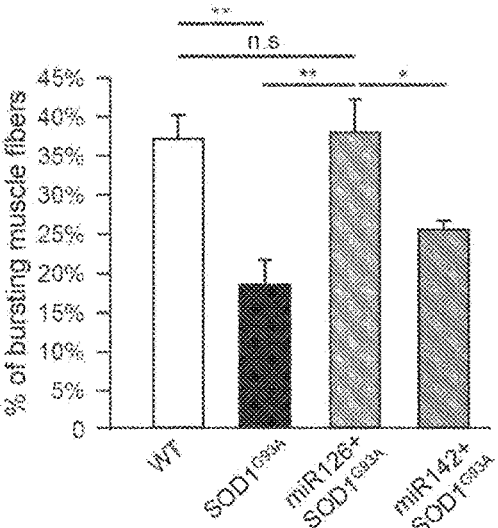
FIG. 4G

MIRI26-5P FOR TREATING MOTOR NEURON DISEASES

FIELD OF THE INVENTION

The present invention relates to methods for treating motor neuron diseases and neuromuscular junction abnormalities. Particularly, the methods comprise increasing miRNA126-5p expression in skeletal muscle cells and/or motor neurons, and/or inhibiting miRNA126-5p expression in glial cells, thereby spatially up-regulating and/or down-regulating miRNA126-5p levels, and thus treating amyotrophic lateral sclerosis.

BACKGROUND OF THE INVENTION

Amyotrophic lateral sclerosis (ALS) is an adult-onset lethal neurodegenerative disease characterized by muscle atrophy and motor neuron death. It affects motor neurons (MNs) in the cortex, brain stem, and spinal cord and is characterized by neuromuscular junction (NMJ) disruption, MN axon degeneration, and neuronal death. ALS is the most common motor neuron disease, with a lifetime risk of approximately 1:400 individuals. Patients diagnosed with ALS typically die within 3-5 years.

About 20% of familial ALS (fALS) is accounted for by mutations in the superoxide dismutase 1 (SOD1). Other mutations found in ALS patients include hexanucleotide expansion repeats in the (9orf72 locus, which lead to various di-peptide repeats, e.g., Proline-Arginine or Glycine-Arginine repeats ($PR_{50}$ and $GR_{50}$, respectively), and in the gene encoding the TDP43 RNA binding protein. The diversity of ALS-related mutations has given rise to the use of numerous animal models with diverse phenotypes, ranging from no effect on motor neuron function to severe progressive paralysis.

The neurodegeneration that occurs in ALS is considered to be a non-cell autonomous process involving interactions between the neuron and its diverse extracellular microenvironments via an unknown mechanism. It is believed that the molecular basis for neuronal dysfunction and death in ALS might be due to alterations in the nature of the extracellular signaling pathways that switch from pro-survival to toxic. It has been shown that multiple tissues outside the CNS, including skeletal muscle, astrocytes, and microglia contribute to ALS pathologies. Alterations in RNA metabolism and microRNAs (miRs) can contribute to, and also be part of mechanisms that initiate the disease (Lemmens et al., 2010; Emde and Hornstein, 2014). MicroRNAs are post-transcriptional regulators that play an important role in many cellular processes, e.g., axon growth and retraction, and were demonstrated to be involved in many diseases including neurodegenerative diseases such as ALS (Hawley et al., 2017; Molasy et al., 2017). Alterations in miR expression profile were identified specifically in axons of ALS models (Rotem et al., 2017), as well as in muscles leading to increasing attempts to either use or target miRs as therapeutic strategies (Di Pietro et al., 2017).

Semaphorin3A (Sema3A) was initially identified as a repellent guidance molecule. However, other studies showed that it can also induce neuronal cell death of sympathetic, sensory, retinal, and cortical neurons. Neuropilin1 (NRP1) has been shown to be the receptor binding component for Sema3A as well as for some other type 3 Semaphorins. Sema3A was found to be up-regulated following central nervous system injury as well as in several neurodegenerative diseases. For example, Sema3A was found to be up-regulated in terminal Schwann cells (TSCs) of the $SOD1^{G93A}$ transgenic mouse model for ALS and in the motor cortex of ALS patients. Moreover and in apparent contradiction to these effects, loss of astrocyte-encoded Sema3 A specifically in the mouse spinal cord leads to dysregulation and death of motor neurons (Molofsky et al., 2014), suggesting that spatial alteration in this pathway plays a role in disease pathology and progression.

Maimon et al. (2017, 2018, and 2019) disclosed that muscle secretion of axon destabilizing type 3 semaphorins regulated by miR126-5p facilitate motor neuron degeneration in ALS and that overexpression of miR126-5p is sufficient to transiently rescue neuromuscular junction disruption and axon degeneration in ALS mice models.

U.S. 2011/0196017 discloses methods of promoting vascular integrity and/or vascular repair comprising administering to a subject at risk of or suffering from vascular damage an agonist of miR-126 function. According to U.S. 2011/0196017, miR-126 is referred to as miR126-3p.

U.S. Pat. No. 9,006,195 discloses methods for increasing blood output in a mammal comprising administering to the mammal miR-125b, miR-126, and/or miR-155 oligonucleotides.

U.S. Pat. No. 9,179,654 discloses methods of inhibiting angiogenesis in a subject comprising administering to the subject an inhibitor of miR-126.

There remains an unmet need for improved methods for treating motor neuron diseases (NMDs), particularly ALS, as well as neuromuscular junction (NMJ) abnormalities.

SUMMARY OF THE INVENTION

The present invention provides pharmaceutical compositions, pharmaceutical combinations, and uses thereof for treating motor neuron diseases (MND) and neuromuscular junction (NMJ) abnormalities.

The present invention provides methods of alleviating, attenuating the progression of, or treating motor neuron diseases (MNDs) or neuromuscular junction (NMJ) abnormalities comprising administering to a subject at risk of having or having the MND or the NMJ abnormality at least one pharmaceutical composition selected from:

(a) a first pharmaceutical composition comprising a therapeutically effective amount of an agent selected from the group consisting of: (i) microRNA (miR) 126-5p as set forth in SEQ ID NO:1, a precursor, a seed, or a homolog thereof; (ii) a polynucleotide encoding miR126-5p as set forth in SEQ ID NO:1, a precursor, a seed, or a homolog thereof; and (iii) an expression vector comprising a polynucleotide encoding miR126-5p as set forth in SEQ ID NO:1, a precursor, a seed, or a homolog thereof; and (b) a second pharmaceutical composition comprising a therapeutically effective amount of a nucleic acid-based inhibitor of miR126-5p, wherein miR126-5p is set forth in SEQ ID NO:1.

According to some embodiments, the methods comprise increasing microRNA126-5p (miR126-5p) expression in skeletal muscle cells and/or motor neurons and/or inhibiting miR126-5p expression in glial cells, the methods comprise administering to a subject having a MND or a NMJ abnormality at least one pharmaceutical composition selected from:

(a) a first pharmaceutical composition comprising a miR126-5p, a polynucleotide encoding miR126-5p, or an expression vector comprising the polynucleotide encoding miR126-5p, wherein the first pharmaceutical composition is effective to increase miR126-5p expression in skeletal muscle cells;

(b) a second pharmaceutical composition comprising miR126-5p, a polynucleotide encoding miR126-5p, or an expression vector comprising the polynucleotide encoding miR126-5p, wherein the second pharmaceutical composition is effective to increase miR126-5p expression in motor neurons; and (c) a third pharmaceutical composition comprising a nucleic-based inhibitor of miR126-5p, wherein the third pharmaceutical composition is effective to inhibit miR126-5p in glial cells.

The present invention is based in part on the unexpected findings that injection of a lentiviral vector encoding miR126-5p and containing skeletal muscle α-actin promoter to the skeletal gastrocnemius (GC) muscle of pre-symptomatic SOD1$^{G93A}$ mice, an animal model of amyotrophic lateral sclerosis (ALS), resulted in a higher innervation rate than that observed with SOD1$^{G93A}$ mice injected with a control lentiviral vector encoding miR-142, as determined in a co-culture system of myocytes and motor neuron axons. Behavioral tests on these SOD1$^{G93A}$ mice to evaluate their motor defects indicated that overexpression of miR126-5p in the skeletal muscles of these animals inhibited the neurodegeneration process and reduced the detrimental effects of muscle-secreted semaphoring (Sema) 3A on motor neuron function in ALS. The protective effect of miR126-5p against neurodegeneration was more prominent at early stages of ALS than at later stages of the disease.

The inventors further disclose herein that overexpression of miR126-5p in SOD1$^{G93A}$ motor neuron cultures, using a lentiviral vector encoding miR126-5p and containing a neuron specific promoter, enhanced neurite growth. Thus, overexpression of miR126-5p in motor neurons, specifically in large-caliber axons of the brain and spinal cord, has a beneficial effect for treating ALS.

It is further disclosed that administration of a first lentiviral vector encoding miR126-5p to the GC muscle of SOD1$^{G93A}$ mice, and administration to the spinal cord of these mice a second lentiviral vector encoding an antisense oligonucleotide of miR126-5p, wherein the first and the second lentiviral vectors contain a skeletal muscle specific promoter and a glial cell specific promoter, respectively, such administrations result in up-regulation of miR126-5p levels in the skeletal muscle cells and in down-regulation of miR126-5p levels in glial cells, leading to an improvement in motor neuron survival and NMJ function in the ALS mice model.

The present invention therefore provides efficient methods of treating or attenuating the progression of MNDs or NMJ abnormalities by spatial manipulation of miR126-5p levels, namely by up-regulating miR126-5p levels in skeletal muscles and/or motor neurons and/or by down-regulating miR126-5p levels in glial cells as compared to miR126-5p levels in these cells in non-treated subjects.

According to one aspect, the present invention provides a pharmaceutical combination for use in treating a motor neuron disease (MND) or a neuromuscular junction (NMJ) abnormality, the pharmaceutical combination comprising at least two pharmaceutical compositions selected from.

(a) a first pharmaceutical composition comprising a therapeutically effective amount of an agent selected from the group consisting of: (i) microRNA (miR) 126-5p, a precursor, a seed, or a homolog thereof; (ii) a polynucleotide encoding miR126-5p, a precursor, a seed, or a homolog thereof; and (iii) an expression vector comprising a polynucleotide encoding miR126-5p, a precursor, a seed, or a homolog thereof, wherein the first pharmaceutical composition is effective to increase miR126-5p expression in a skeletal muscle cell;

(b) a second pharmaceutical composition comprising a therapeutically effective amount of an agent selected from the group consisting of: (i) miR126-5p, a precursor, a seed, or a homolog thereof; (ii) a polynucleotide encoding miR126-5p, a precursor, a seed, or a homolog thereof; and (iii) an expression vector comprising a polynucleotide encoding miR126-5p, a precursor, a seed, or a homolog thereof, wherein the second pharmaceutical composition is effective to increase miR126-5p expression in a motor neuron; and (c) a third pharmaceutical composition comprising a therapeutically effective amount of a nucleic acid-based inhibitor of miR126-5p, wherein the third pharmaceutical composition is effective to inhibit miR126-5p expression in a glial cell.

According to some embodiments, the pharmaceutical combination comprises two pharmaceutical compositions selected from the group consisting of the first, second, and third pharmaceutical compositions. According to additional embodiments, the pharmaceutical combination comprises the first and the second pharmaceutical compositions.

According to further embodiments, the pharmaceutical combination comprising the following pharmaceutical compositions:

(a) a first pharmaceutical composition comprising a therapeutically effective amount of an expression vector comprising a polynucleotide encoding miR126-5p, a precursor, a seed, or a homolog thereof, wherein the first pharmaceutical composition is effective to increase miR126-5p expression in a skeletal muscle cell; and (b) a second pharmaceutical composition comprising a therapeutically effective amount of an expression vector comprising a polynucleotide encoding miR126-5p, a precursor, a seed, or a homolog thereof, wherein the second pharmaceutical composition is effective to increase miR126-5p expression in a motor neuron.

According to some embodiments, the MND is selected from the group consisting of Amyotrophic Lateral Sclerosis (ALS), primary lateral sclerosis, progressive muscular atrophy, pseudobulbar palsy, progressive bulbar palsy, lower motor neuron disease, and spinal muscular atrophy (SMA). According to a certain embodiment, the MND is ALS. According to additional embodiments, the ALS is selected from the group consisting of sporadic ALS (sALS) and familial ALS (fALS).

According to further embodiments, the MNJ abnormality is selected from the group consisting of Myasthenia Gravis, Lambert-Eaton syndrome, muscular dystrophy, and peripheral nerve injuries.

According to an exemplary embodiment, miR126-5p comprises or consists of the nucleotide sequence as set forth in SEQ ID NO:1. According to still further embodiments, the precursor of miR126-5p is pre-miR126-5p as set forth in SEQ ID NO:2.

According to still further embodiments, the agent is an expression vector comprising a polynucleotide encoding miR126-5p as set forth in SEQ ID NO:1.

According to yet further embodiments, the nucleic-acid based inhibitor of miR126-5p is an antisense oligonucleotide of miR126-5p or an expression vector comprising a polynucleotide sequence encoding the antisense oligonucleotide.

According to still further embodiments, the nucleic-acid based inhibitor of miR126-5p comprises an oligonucleotide that forms a duplex with miR126-5p or an expression vector comprising a nucleotide sequence encoding the oligonucleotide.

According to additional embodiments, the expression vector is a viral vector. According to further embodiments, the viral vector is selected from the group consisting of lentiviral vectors and adeno-associated (AAV) viral vectors. According to yet further embodiments, the lentiviral vector is selected from the group consisting of an HIV-based lentiviral vector, an EIAV-based lentiviral vector, and self-inactivating (SIN) lentiviral vector.

According to some embodiment, the expression vector of the first pharmaceutical composition further comprises a muscle specific promoter. According to further embodiments, the muscle specific promoter is a skeletal muscle specific promoter. According to additional embodiments, the muscle specific promoter is selected from the group consisting of skeletal muscle α-actin promoter, myogenin promoter, and muscle creatine kinase promoter.

According to further embodiments, the expression vector of the second pharmaceutical composition further comprises a neuron specific promoter. According to yet further embodiments, the neuron specific promoter is selected from the group consisting of neurofilament promoter, such as neurofilament heavy polypeptide promoter, synapsin promoter, calcitonin gene-related peptide (CGRP) promoter, choline acetyl transferase (ChAT) promoter, neuron specific enolase (NSE) promoter, Thy-1 promoter, and HB9 promoter.

According to still further embodiments, the nucleic acid-based inhibitor of miR126-5p is an expression vector comprising a polynucleotide encoding said nucleic acid-based inhibitor of miR126-5p, wherein the expression vector further comprising a glial cell specific promoter. According to yet further embodiments, the glial cell specific promoter is selected from the group consisting of glial fibrillary acidic protein (GFAP) promoter, glutamine synthase (GS) promoter, Olig1-3 promoters, MAG promoter, MOG promoter, MBP promoter, and S100ß promoter.

According to some embodiments, the pharmaceutical combination comprising the following pharmaceutical compositions:

(a) a first pharmaceutical composition comprising a therapeutically effective amount of a lentiviral vector comprising a polynucleotide encoding miR126-5p, a precursor, a seed, or a homolog thereof, preferably miR126-5p comprises or consists of SEQ ID NO: 1, wherein the lentiviral vector further comprising skeletal muscle α-actin promoter, and wherein the first pharmaceutical composition is effective to increase miR126-5p expression in a skeletal muscle cell; and (b) a second pharmaceutical composition comprising a therapeutically effective amount of a lentiviral vector comprising a polynucleotide encoding miR126-5p, a precursor, a seed, or a homolog thereof, preferably miR126-5p comprises or consists of SEQ ID NO: 1, wherein the expression vector further comprising neurofilament promoter, and wherein the second pharmaceutical composition is effective to increase miR126-5p expression in a motor neuron.

According to some embodiments, the first pharmaceutical composition is formulated for intramuscular injection, preferably for intramuscular injection into a skeletal muscle tissue. Alternatively, the first pharmaceutical composition is formulated for subcutaneous, intravenous or intraarterial injection, preferably at or near a skeletal muscle tissue.

According to further embodiments, the second and/or third pharmaceutical compositions are each formulated for injection or infusion, preferably into the spinal cord or CNS. According to still further embodiments, the second or third pharmaceutical compositions are each administered via intrathecal or intracerebroventricular route of administration.

According to additional embodiments, the first pharmaceutical composition is administered prior to, concomitant with, and/or after administering the second pharmaceutical composition. According to further embodiments, the first pharmaceutical composition is administered prior to, concomitant with, and/or after administering the third pharmaceutical composition. According to still further embodiments, the first pharmaceutical composition is administered prior to, concomitant with, and/or after administering the second and the third pharmaceutical compositions.

According to yet further embodiments, the first, second and third pharmaceutical compositions are each administered once a day, twice a week, once a week, twice a month, once a month, once in several months, twice a year, once a year, or as required until one or more symptoms of the MND or NMJ abnormality disappears or decreases. According to specific embodiments, the expression vectors according to the invention are administered once in several months, such as once or twice a year, or less frequently.

According to another aspect, the present invention provides a method of treating a motor neuron disease (MND) or a neuromuscular junction (NMJ) abnormality, the method comprising administering to a subject having the MND or NMJ abnormality at least one pharmaceutical composition selected from:

a first pharmaceutical composition comprising an agent selected from the group consisting of: (i) microRNA (miR) 126-5p, a precursor, a seed, or a homolog thereof; (ii) a polynucleotide encoding miR126-5p, a precursor, a seed, or a homolog thereof; and (iii) an expression vector comprising a polynucleotide encoding miR126-5p, a precursor, a seed, or a homolog thereof, wherein the first pharmaceutical composition is effective to increase miR126-5p expression in a skeletal muscle cell;

a second pharmaceutical composition comprising an agent selected from the group consisting of: (i) miR126-5p, a precursor, a seed, or a homolog thereof; (ii) a polynucleotide encoding miR126-5p, a precursor, a seed, or a homolog thereof; and (iii) an expression vector comprising a polynucleotide encoding miR126-5p, a precursor, a seed, or a homolog thereof, wherein the second pharmaceutical composition is effective to increase miR126-5p expression in a motor neuron; and a third pharmaceutical composition comprising a nucleic-acid based inhibitor of miR126-5p, wherein the third pharmaceutical composition is effective to inhibit miR126-5p expression in a glial cell, according to the principles of the present invention.

According to one exemplary embodiment, the method comprises administering to the subject having the MND or the NMJ abnormality the first pharmaceutical composition only.

According to some embodiments, the method comprises administering to the subject at least two pharmaceutical compositions selected from the first, the second and the third pharmaceutical compositions.

According to additional embodiments, the method comprises administering to the subject at least two pharmaceutical compositions selected from:

a first pharmaceutical composition which comprises an expression vector comprising a polynucleotide encoding miR126-5p, a precursor, a seed, or a homolog thereof, the first pharmaceutical composition is effective to increase miR126-5p expression in a skeletal muscle cell;

a second pharmaceutical composition which comprises an expression vector comprising a polynucleotide encoding miR126-5p, a precursor, a seed, or a homolog thereof, wherein the second pharmaceutical composition is effective to increase miR126-5p expression in a motor neuron; and a third pharmaceutical composition which comprises an expression vector comprising a polynucleotide encoding a nucleic-acid based inhibitor of miR126-5p, wherein the third pharmaceutical composition is effective to inhibit miR126-5p expression in a glial cell, according to the principles of the present invention.

According to further embodiments, the method comprises administering to the subject the first and the second pharmaceutical compositions according to the principles of the present invention.

According to a further aspect, the present invention provides an expression vector or a pharmaceutical composition comprising the expression vector, wherein the expression vector comprises a polynucleotide encoding miR126-5p, a precursor, a seed, or a homolog thereof, wherein said expression vector further comprising a tissue specific promoter selected from the group consisting of skeletal muscle specific promoters and neuron specific promoters.

According to some embodiments, the vector is a viral vector. According to additional embodiments, the viral vector is a lentiviral vector or an adeno-associated viral vector. According to further embodiments, the lentiviral vector is selected from the group consisting of an HIV-based lentiviral vector, an EIAV-based lentiviral vector, and self-inactivating (SIN) lentiviral vector.

According to an exemplary embodiment, the skeletal muscle specific promoter is skeletal muscle α-actin promoter. According to another exemplary embodiment, the neuron specific promoter is neurofilament promoter, preferably neurofilament heavy polypeptide promoter. According to additional embodiments, miR126-5p comprises or consists of the nucleotide sequence as set forth in SEQ ID NO:1.

According to an additional aspect, the present invention provides an expression vector or a pharmaceutical composition comprising the expression vector, wherein the expression vector comprises a nucleotide sequence encoding an antisense oligonucleotide of miR126-5p as set forth in SEQ ID NO:1, said expression vector further comprising a glial cell specific promoter. According to an exemplary embodiment, the glial cell specific promoter is glial fibrillary acidic protein (GFAP) promoter.

According to another aspect, the present invention provides an expression vector or a pharmaceutical composition comprising the expression vector, wherein the expression vector comprises a nucleotide sequence encoding an oligonucleotide that forms a duplex with miR126-5p, said expression vector further comprising a glial cell specific promoter. According to an exemplary embodiment the glial cell specific promoter is GFAP promoter.

These and other embodiments of the present invention will become apparent in conjunction with the figures, description and claims that follow.

BRIEF DESCRIPTION OF THE FIGURES

FIGS. 1A-B show western-blot analysis of P30 and P60 GC muscle extracts levels of Sema3A in pre-symptomatic SOD1$^{G93A}$ muscles compared with their corresponding LM control. FIG. 1C shows qPCR analysis of pre-symptomatic P60 and P30 GC muscle extracts of Sema3A in SOD1$^{G93A}$. FIG. 1D shows Sema3A intensity as analyzed from immunostaining of SOD1$^{G93A}$ primary myocytes after 7 days in culture. FIG. 1E shows Sema3A western blot analysis of SOD1$^{G93A}$ primary myocyte-conditioned media. FIG. 1F shows the percentage of muscle fibers expressing Sema3A in their NMJs as analyzed from immunostaining of fixed whole SOD1$^{G93A}$ P60 GC muscles. FIG. 1G shows western blot analysis of NRP1 levels in GC muscle extracts from P60 SOD1$^{G93A}$ mice. FIG. 1H shows western blot analysis of NRP1 levels of sciatic nerve (SN) extract from P60 SOD1$^{G93A}$ mice. FIG. 1I shows western blot analysis of NRP1 levels of primary SOD1$^{G93A}$ MN lysates after 3 days in culture. FIGS. 1J-K shows NRP1 levels in the axons and Somata analyzed from immunostaining of SOD1$^{G93A}$ primary MNs after 3 days in culture. FIG. 1L shows the percentage of muscle fibers expressing NRP1 in NMJs as analyzed from immunostaining of fixed whole P60 SOD1$^{G93A}$ GC muscles.

FIG. 2A shows the experimental procedure illustration of a microfluidic chamber with no muscles after applying Sema3A to the distal compartment. FIG. 2B shows quantification of the rate of degraded axons in the distal compartment. FIG. 2C shows schematic view of the experimental procedure in FIGS. 2D-E. HB9:: GFP spinal cord explants and primary myocytes of SOD1$^{G93A}$, TDP43$^{A315T}$, C9orf72-PR$_{50}$, C9orf72-GR$_{50}$, or LM, GFP, and SOD1wt as controls were co-cultured in a microfluidic chamber and the growth of HB9::GFP axons was assessed by time-lapse imaging of the microgroove compartment. FIG. 2D shows quantification of the rate of axons traversing the distal compartment—the mean percentage of axons that traversed the distal compartment out of the total axons in each field. FIG. 2E shows quantification of the mean percentage of axons that traversed the distal compartment out of the total number of axons in each field in co-culture with TDP43$^{A315T}$, C9orf72-PR$_{50}$, C9orf72-GR$_{50}$ myocytes, or GFP as a control. FIG. 2F shows quantification of the rate of degenerated SOD1$^{G93A}$ axons in the distal compartment treated with control CM, SOD1$^{G93A}$ CM, or SOD1$^{G93A}$ CM that was co-incubated with anti-NRP1 antibody, as analyzed from immunostaining.

FIGS. 3A-G show miR126-5p is depleted in SOD1$^{G93A}$ muscles and regulates Sema3 and NRP expression. FIG. 3A shows miR126-5p levels in SOD1$^{G93A}$ muscles. FIG. 3B shows qPCR analysis of miR126-5p in SOD1$^{G93A}$ P60 GC muscle extracts. FIGs. C-F show qPCR analysis of Sema3A, NRP1, Sema3B, and NRP2 transcript levels in Hela cells overexpressing either miR126-5p or miR142. FIG. 3G shows impedance recording of U87MG live cells overexpressing miR126-5p or miR142 with Sema3 A added to the culture medium.

FIGS. 4A-G show that overexpression of miR126-5p in primary SOD1$^{G93A}$ myocytes blocks motor axon degeneration and preserves neuromuscular junction activity in a compartmental co-culture. FIGS. 4A-B show western blot analysis of transfected myocyte extract overexpressing miR126-5p or miR142 and their conditioned media. FIG. 4C shows schematic view of the experimental procedure in (D-E). HB9::GFP spinal cord explants and primary myocytes of SOD1$^{G93A}$ mice were co-cultured in a microfluidic chamber. The growth of the HB9::GFP axons was assessed both by time-lapse imaging of the microgroove compartment and by imaging axons that traversed the distal compartment. FIG. 4D shows quantification of time-lapse images of HB9::GFP axon growth when co-cultured with SOD1$^{miR126}$ or SOD1$^{miR142}$ myocytes. FIG. 4E shows quantification of HB9::GFP axon growth when co-cultured with PR$_{50}$$^{miR126}$ or PR$_{50}$miR$^{142}$ myocytes. FIG. 4F shows representative myocyte contraction plot showing the bursting contractile behavior of innervated myocytes in vitro. FIG. 4G shows quantification of the percentage of innervated myocytes that contract in a bursting pattern in SOD1$^{G93A}$, SOD1$^{miR126}$ and SOD1$^{miR142}$ myocytes compared with LM controls.

FIG. 5A shows schematic view of the in-vivo experimental procedure. SOD1$^{G93A}$ mice were injected with either pLL-eGFP-miR126-5p or pLL-eGFP-miR142 in their right or left GC muscles, respectively. FIG. 5B shows the percentage of innervated NMJs in muscles as analyzed from immunostaining of ~P90 and P120 SOD1$^{G93A}$ GC muscles injected with either miR126-5p or miR142 lentiviral vectors. FIG. 5C shows semi-quantification of the minimal muscle fiber diameter of a GC cross section analyzed from histological H&E staining images of P120 WT, SOD1$^{G93A}$, miR126-5p, and miR142. FIG. 5D shows illustration of the CatWalk XT gait analysis system that monitors mouse footprints. FIG. 5E shows gait analysis Mean Stand Index parameter that indicates the speed at which the paw loses contact with the surface in SOD1$^{G93A}$ P90 miR126-5p or miR142 injected limbs. FIG. 5F shows the gait analysis percent single support parameter which indicates the relative duration of contact of a single paw on the glass floor of WT, SOD1$^{G93A}$ and injected mice. FIG. 5G shows Gait analysis base of support parameter that indicates the average width between the hind paws of P90 and P120 mice.

INCORPORATION BY REFERENCE OF SEQUENCE LISTING

Figure 1A:
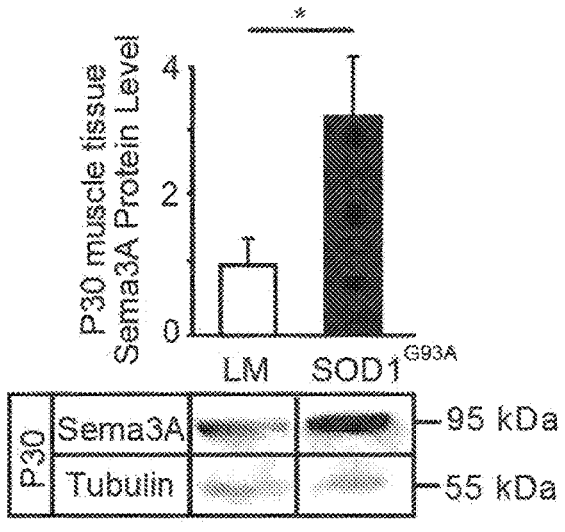
FIGS. 1A-L show elevation in the levels of Sema3A and NRP1 in pre-symptomatic ALS mutated mice.

The Sequence Listing, submitted as a separate electronic file entitled 'RAMOT-084 PCT Sequence Listing_ST25.txt' and created in compliance with 37 CFR 1.821 (c) (1), is incorporated herein by reference as part of the specification. The Sequence Listing provides the nucleotide sequences disclosed in this application.

DETAILED DESCRIPTION OF THE INVENTION

The present invention provides pharmaceutical compositions and pharmaceutical combinations for use in alleviating, attenuating the progression of, or treating motor neuron diseases (MNDs) or neuromuscular junction (NMJ) abnormalities, the pharmaceutical compositions are selected from:

(a) a first pharmaceutical composition comprising a microRNA (miR) 126-5p oligonucleotide, a polynucleotide encoding same, or an expression vector comprising the polynucleotide encoding miR126-5p, wherein the first pharmaceutical composition is effective to increase miR126-5p expression in a skeletal muscle cell;

(b) a second pharmaceutical composition comprising a miR126-5p oligonucleotide, a polynucleotide encoding same, or an expression vector comprising the polynucleotide encoding miR126-5p, wherein the second pharmaceutical composition is effective to increase miR126-5p expression in a motor neuron; and (c) a third pharmaceutical composition comprising a nucleic-based inhibitor of miR126-5p or an expression vector comprising a polynucleotide encoding same, wherein the third pharmaceutical composition is effective to inhibit miR126-5p expression in a glial cell.

The present invention is based in part on the unexpected findings that skeletal muscles of SOD1$^{G93A}$ mice, an animal model of amyotrophic lateral sclerosis (ALS), secreted high levels of Semaphorin3A (Sema3A) as compared to skeletal muscles of control mice. Sema3A was shown by the inventors to trigger motor neuron (MN) axon degeneration in a co-culture system of myocytes and motor neuron cells. The inventors show herein that addition of a blocking antibody of Neuropilin1 (NRP1) to myocytes of SOD1$^{G93A}$ mice protected MN axon degeneration in the co-culture system only partially, implying that ALS muscles secrete other destabilizing factors, and therefore MN axon degeneration cannot be blocked by targeting Sema3A alone.

It is now disclosed that miR126-5p specifically targets Sema3A, NRP1, Sema3B and NRP2. Surprisingly, transfection of myocytes from two animal models of ALS with a lentiviral vector encoding miR126-5p and containing a skeletal muscle specific promoter showed that the myocytes did not facilitate MN axon degeneration, but rather manifested axon growth. Moreover, injection of the lentiviral vector encoding miR126-5p to the skeletal gastrocnemius (GC) muscle of pre-symptomatic SOD1$^{G93A}$ mice resulted in a higher innervation rate than that observed with SOD1$^{G93A}$ mice injected with a lentiviral vector encoding miR-142 as a control, as determined in a co-culture system of myocytes and motor neuron axons. Behavioral tests on these SOD1$^{G93A}$ mice to evaluate their motor defects indicated that overexpression of miR126-5p in the skeletal muscles of these animals inhibited the neurodegeneration process and reduced the detrimental effects of muscle-secreted Sema3A on motor neuron function in ALS. The protective effect of miR126-5p against neurodegeneration was more prominent at early stages of ALS than at later stages of the disease.

The inventors further show herein that overexpression of miR126-5p in SOD1$^{G93A}$ motor neuron cultures, using a lentiviral vector encoding miR126-5p and containing a neuron specific promoter, enhanced neurite growth. Thus, overexpression of miR126-5p in motor neurons has a beneficial effect for treating ALS.

For convenience and clarity certain terms employed in the specification, examples, and claims are described herein.

Definitions

The term "microRNA", "miRNA", and "miR" are synonymous and refer to a collection of non-coding single-stranded RNA molecules of about 19-28 nucleotides in length, which regulate gene expression. miRNAs are found in a wide range of organisms (e.g. viruses, humans) and have been shown to play a role in development, homeostasis, and disease etiology.

The term "treating" and "treatment" as used herein refers to abrogating, inhibiting, slowing or reversing the progression of a disease or condition, alleviating or ameliorating one or more clinical symptoms of a disease or condition, or preventing the appearance of clinical symptoms of a disease or condition. The term "preventing" is defined herein as barring a subject from acquiring a disease or condition.

The term "motor neuron disease (MND)" as used herein, refers to a neurological disorder that selectively destroys motor neurons of the central nervous system. NMD is attributed to degenerative changes in the motor neuron pathway.

The term "neuromuscular junction (NMJ) abnormality" refers to a disorder which is characterized by changes in the morphology of the NMJ and by impairment in neuromuscular transmission. The NMJ abnormality may involve muscle distortion and muscle de- or re-innervation.

As used herein, the term "subject" refers to a human being of any gender or age (e.g., infant, child or adult) who has been diagnosed with MND or NMJ abnormality or is predisposed to MND or NMJ abnormality. The subject may show preliminary signs of a MND or NMJ abnormality, such as muscle fatigue or have a moderate or full blown late stage disease. Alternatively, the subject may have a genetic predisposition to the disease. This term also encompasses a subject who is symptomatic as well as a subject who is asymptomatic. In some embodiments, the subject is a human afflicted with MND or NMJ abnormality. In some embodiments, the subject is at risk of developing MND or NMJ abnormality. In other embodiments, the subject has already developed MND or NMJ abnormality.

The terms "expression vector" and "expression construct" are used herein interchangeably and refer to an artificially assembled or isolated nucleic acid molecule which includes one or more nucleic acid sequences, wherein the nucleic acid sequences may include coding sequences (that is, a sequence which encodes an end product), regulatory sequences, non-coding sequences, or any combination thereof. The expression vector or expression construct include, for example, a viral vector but should not be seen as being limited thereto. The terms "expression vector" and "expression construct" refer to a vector that harbors the nucleic acid sequence of interest for being expressed in a target cell.

The term "polynucleotide" refers to a single-stranded or double-stranded oligomer or polymer of ribonucleic acid (RNA), deoxyribonucleic acid (DNA) or mimetics thereof. This term includes polynucleotides and/or oligonucleotides derived from naturally occurring nucleic acid molecules (e.g., RNA or DNA), synthetic polynucleotide and/or oligonucleotide molecules composed of naturally occurring bases, sugars, and covalent internucleoside linkages (e.g., backbone), as well as synthetic polynucleotides and/or oli-gonucleotides having non-naturally occurring portions, which function similarly to respective naturally occurring portions.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules, or mimic precursors (e.g., pre-miRNAs or pri-miRNAs). miRNA mimics can be comprised of modified or unmodified RNA, DNA, RNA-DNA hybrids, or alternative nucleic acid chemistries. For mature or double stranded miRNA mimics, the length of the oligonucleotide can vary between 13-40, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides.

As used herein a "pharmaceutical composition" refers to a preparation of one or more of the active agents described herein with other chemical components such as pharmaceutically acceptable carriers and excipients. The purpose of a pharmaceutical composition is to facilitate administration of an active agent to an organism.

The term "pharmaceutically acceptable carrier" refers to a carrier or a diluent that does not cause significant irritation to an organism and does not abrogate the biological activity and properties of the administered active agent. An adjuvant is included under these phrases.

The term "excipient" refers to an inert substance added to a pharmaceutical composition to further facilitate administration of an active agent. Examples, without limitation, of excipients include calcium carbonate, calcium phosphate, various sugars, types of starch, cellulose derivatives, gelatin, vegetable oils and polyethylene glycols.

The term "partially complementary" refers to a sequence that is at least about 75%, 80%, 85%, 90%, 95%, 96%, 97%, 98%, or 99% complementary to a target polynucleotide sequence.

As used herein the term "about" refers to +10% of the indicated numerical value.

It is to be understood that each possibility disclosed throughout the specification represents a separate embodiment of the invention.

microRNAs

Genes coding for miRNAs are transcribed to produce a miRNA precursor known as the pri-miRNA. The pri-miRNA is typically part of a polycistronic RNA comprising multiple pri-miRNAs. The pri-miRNA may form a hairpin with a stem and loop. The stem may comprise mismatched bases.

The hairpin structure of the pri-miRNA is recognized by Drosha, which is an RNase III endonuclease. Drosha typically recognizes terminal loops in the pri-miRNA and cleaves approximately two helical turns into the stem to produce a 60-70 nucleotide precursor known as the pre-miRNA. Drosha cleaves the pri-miRNA with a staggered cut typical of RNase III endonucleases yielding a pre-miRNA stem loop with a 5' phosphate and approximately 2 nucleotide 3' overhang. It is estimated that approximately one helical turn of stem (approximately 10 nucleotides) extending beyond the Drosha cleavage site is essential for efficient processing. The pre-miRNA is then actively transported from the nucleus to the cytoplasm by Ran-GTP and the export receptor Ex-portin-5.

The double-stranded stem of the pre-miRNA is then recognized by Dicer, which is also an RNase III endonuclease. Dicer may also recognize the 5' phosphate and 3' overhang at the base of the stem loop. Dicer then cleaves off the terminal loop two helical turns away from the base of the stem loop leaving an additional 5' phosphate and approximately 2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs. Although initially present as a double-stranded species with miRNA*, the miRNA eventually becomes incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded into the RISC.

When the miRNA strand of the miRNA:miRNA* duplex is loaded into the RISC, the miRNA* is usually removed and degraded, however in some cases both strands can be active. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity. It is to be understood that the designation miRNA and miRNA* is interchangeable with the designation miRNA-5p and miRNA-3p or vice versa. The inventors of the present invention refer to miR126-5p as playing an important role in regulating semaphorin 3 levels in muscles and hence in protecting from axonal degeneration.

The RISC identifies target nucleic acids based on high levels of complementarity between the miRNA and the mRNA, especially by nucleotides 2-8 of the miRNA. These nucleotides also known as the "seed" sequence of the miRNA and is considered to be essential for the binding of the miRNA to the mRNA.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA.

Information concerning miRNA oligonucleotides and the precursor's pri-miRNA and pre-miRNA sequences is available in miRNA databases such as miRBase, Target scan, and the NCBI human genome database.

It will be appreciated that introducing into cells (e.g., human cells) a miRNA according to some embodiments of the present invention can be performed in a number of ways:

1. Transiently transfecting the cells with a mature double stranded miRNA;

2. Stably or transiently transfecting the cells with an expression vector which encodes the mature miR126-5p as set forth in SEQ ID NO: 1 (5'-CAUUAUUAC-UUUUGGUACGCG-3') or the mature miR126-3p as set forth in SEQ ID NO:3 (5'-UCGUACCGUG-AGUAAUAAUGCG-3'); 3. Stably or transiently transfecting the cells with an expression vector which encodes the pre-miR126 as set forth in SEQ ID NO: 2 (5'-CGCUGGCGACGGGACAUUAUUACUUUUG-GUACGCGCUGUGACACUUCAAACUCGU ACCGUGAGUAAUAAUGCGCCGUCCACGGCA-3'). The pre-miRNA sequence may comprise from 45-90, 60-80 or 60-70 nucleotides. The sequence of the pre-miR126 can comprise a miR126-5p and a miR126-3p as set forth herein above.

4. Stably or transiently transfecting the cells with an expression vector which encodes the pri-miRNA. The pri-miRNA sequence may comprise from 45-30,000, 50-25,000, 100-20,000, 1,000-1,500 or 80-100 nucleotides. The sequence of the pri-miRNA may comprise a pre-miRNA, miRNA-5p and miRNA-3p, as set forth herein, and variants thereof.

According to one embodiment, the miR126-5p has a nucleotide sequence as set forth in SEQ ID NO:1. Homologs of miR-126-5p can be found under accession number MIMAT0000445 at the miRbase. Homologs of miR126-5p have a nucleotide sequence which is at least 75% identical to SEQ ID NO:1, alternatively at least 80%, 85%, 90%, 95% or 99% identical to SEQ ID NO:1.

Expression vectors typically contain a variety of "control sequences," which refer to nucleic acid sequences necessary, for example, for the transcription of an operably linked coding or non-coding sequence in a particular host organism. In addition to control sequences, expression vectors may contain nucleic acid sequences that serve other functions as well. In some embodiments, an expression vector can be used to encode one or more miRNA molecules in a target cell.

Preparation of miRNAs or miRNA mimics can be effected by chemical synthesis methods or by recombinant methods.

According to a specific embodiment, miR126-5p is used to down-regulate the expression of a gene product (e.g., Sema3A, Sema3B, and/or neurophilins).

Down-regulation of expression may be either transient or permanent.

According to specific embodiments, downregulating expression refers to the absence of mRNA and/or protein, as detected by RT-PCR or Western blot, respectively.

According to some embodiments, down-regulating expression refers to a decrease in the level of mRNA and/or protein, as detected by RT-PCR or Western blot, respectively. The reduction may be by at least 10%, at least 20%, at least 30%, at least 40%, at least 50%, at least 60%, at least 70%, at least 80%, at least 90%, at least 95% or at least 99% reduction in the level of mRNA and/or protein, e.g., Sema3A, in a skeletal muscle cell or tissue as compared to non-treated skeletal muscle cell or tissue.

The prior art teaches of a number of delivery strategies which can be used to efficiently deliver oligonucleotides into a wide variety of cell types.

As mentioned above, agents of the present invention which are capable of up-regulating an activity or amount of miRNA126-5p include, but are not limited to, modified or unmodified polynucleotides (including oligonucleotides of miR126-5p, seed, precursors of miR126-5p, homologs of miR126-5p, and polynucleotide sequences encoding same).

Agonists of miR126-5p will generally take one of three forms. First, there is miR126-5p itself. Such molecules may be delivered to target cells, for example, by injection or infusion, optionally in a delivery vehicle such as a lipid, such as a liposome or lipid emulsion. Second, one may use expression vectors that drive the expression of miR126-5p. The composition and construction of various expression vectors is known in the art and also described herein.

The polynucleotides (including oligonucleotides) designed according to the teachings of the present invention can be generated according to any oligonucleotide synthesis method known in the art, including enzymatic syntheses or solid-phase syntheses. Any other means for such synthesis may also be employed; the actual synthesis of the oligonucleotides is well within the capabilities of one skilled in the art and can be accomplished via established methodologies.

The polynucleotide of the present invention may be modified using various methods known in the art. However, measures are taken to ensure that the miRNA function is maintained.

For example, the oligonucleotides or polynucleotides of the present invention may comprise heterocylic nucleosides consisting of purines and pyrimidines bases, bonded in a 3'-to-5' phosphodiester linkage.

Oligonucleotides or polynucleotides may be modified either in backbone, internucleoside linkages, or bases.

Oligonucleotides or polynucleotides of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include, but are not limited to, other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine.

In some embodiments, the miRNA molecules may be modified at the base moiety, sugar moiety, or phosphate backbone, for example, in order to improve stability of the molecule, hybridization, transport into the cell, and the like. In addition, modifications can be made to reduce susceptibility to nuclease degradation. The miRNA molecules may have other appended groups such as peptides (for example, for targeting host cell receptors in vivo), or agents facilitating transport across the cell membrane or the blood-brain barrier, hybridization-triggered cleavage agents or intercalating agents. Various other well known modifications can be introduced as a means of increasing intracellular stability and half-life. Possible modifications include, but are not limited to, the addition of flanking sequences of ribo- or deoxy-nucleotides to the 5' and/or 3' ends of the molecule. In some circumstances where increased stability is desired, nucleic acids having modified internucleoside linkages such as 2'-O-methylation may be used. Nucleic acids containing modified internucleoside linkages may be synthesized using reagents and methods that are well known in the art.

It will be appreciated that an RNA molecule can be also generated using recombinant techniques.

To express an exogenous polynucleotide (i.e., to produce an miRNA molecule), a nucleic acid sequence encoding the oligonucleotide of the present invention is preferably ligated into a nucleic acid construct, also termed herein "an expression vector". Such a nucleic acid construct includes a promoter sequence for directing transcription of the polynucleotide sequence in the cell in a constitutive or inducible manner.

The nucleic acid constructs or expression vectors of the present invention include additional sequences which render these vectors suitable for replication and integration in eukaryotes (e.g., shuttle vectors). In addition, typical cloning vectors may also contain a transcription and translation initiation sequence, transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized in the expression vector of the present invention is active in a specific cell population transformed.

Of particular interest are muscle specific promoters, which include the α-actin promoter, the myosin light chain-2 promoter, the troponin 1 promoter; the Na/Ca2 exchanger promoter, the dystrophin promoter, the α-integrin promoter, and the muscle creatine kinase (MCK) promoter. According to an exemplary embodiment, the muscle specific promoter is skeletal muscle α-actin promoter.

Neuron specific promoters include, but are not limited to, neurofilament promoter, such as neurofilament heavy polypeptide promoter, Thy-1 promoter, HB9 promoter, and synapsin promoter.

Various methods can be used to introduce the expression vector of the present invention into cells. Such methods are generally described in Sambrook et al., Molecular Cloning: A Laboratory Manual, Cold Springs Harbor Laboratory, New York (1989, 1992).

Nucleic-acid based miR126-5p inhibitors

The present invention further provides "inhibitors of miR126-5p" or "miR126-5p inhibitors" for use in inhibiting miR126-5p expression and/or activity. According to the present invention, the miR126-5p inhibitors are "nucleic acid-based" inhibitors of miR126-5p that are capable of forming a duplex with miR126-5p by Watson-Crick type base pairing.

Any nucleic acid-based inhibitor that is capable of forming a duplex with miR126-5p, i.e. with SEQ ID NO:1, in a glial cell, and inhibiting miR26-5p function can be used in accordance with the present invention, regardless of the actual mechanism by which the inhibitor works. For example, it is possible that a nucleic acid-based inhibitor of miR126-5p may form a duplex with miR126-5p sequences and prevent proper processing of the mature miR126-5p product from its precursor, or may prevent the mature miR126-5p from binding to its target gene, or may lead to degradation of miR126-5p, or may act through some other mechanism. In some embodiments, the nucleic acid-based miR126-5p inhibitors of the invention are antisense oligonucleotides. In a certain embodiment, the nucleic acid-based miR126-5p inhibitors of the invention inhibit neurodegeneration of motor neurons in the spinal cord and CNS in vivo.

As described above, the nucleic acid-based miR126-5p inhibitors of the invention are capable of forming a duplex with miR126-5p, i.e. with SEQ ID NO:1, under cellular conditions. In a preferred embodiment, the miR126-5p inhibitors of the invention are 100% complementary to SEQ ID NO. 1, or comprise a string of 12-25 contiguous nucleotides that are 100% complementary to SEQ ID NO. 1. For example, a preferred miR126-5p inhibitor that is 100% complementary to illustrated miR126-5p is in SEQ ID NO:4 (5'-GTAATAATGAAAACCATGCGC-3'). The miR126-5p inhibitors of the present invention can comprise deoxyri-boynucleotides or ribonucleotides, or modified derivatives or variants of deoxyriboynucleotides or ribonucleotides.

It is well known in the art that while in deoxyribonucleic acids the complementary nucleotide to Adenosine ("A") is thymidine ("T"), in ribonucleic acids the complementary nucleotide to A is uracil ("U"). Thus, the nucleotide T in a deoxyribonucleic acid is the equivalent of the nucleotide U in a ribonucleic acid, and vice versa.

Accordingly, because the miR126-5p inhibitors of the present invention can comprise or consist of either deoxy-riboynucleotides or ribonucleotides, it is to be understood that every miR126-5p inhibitor sequence that is illustrated as comprising the deoxyribonucleotides A, C, T, and G, can equally comprise the ribonucleotides A, C, U, and G, where every position that is a T in the deoxyribonucleotide is substituted with a U in the ribonucleotide version, and vice versa.

In some embodiments, the miR126-5p inhibitors of the invention are not 100% complementary to SEQ ID NO. 1, or do not comprise a string of 12-22 contiguous nucleotides that are 100% complementary to SEQ ID NO. 1, but instead contain some mismatched bases. It is not necessary that there be perfect complementarity between the miR126-5p inhibitor and miR126-5p. Thus, these miR126-5p inhibitors can have one or more regions of non-complementarity with miR-126 flanked by one or more regions of complementarity sufficient to allow duplex formation. It is preferred that the regions of complementarity be at least 8, 9, or 10 nucleotides long. In a preferred embodiment, the nucleic-acid based miR126-5p inhibitors of the invention are "substantially complementary" to, or comprise one or more regions that are "substantially complementary" to SEQ ID NO:1, or a frag-ment thereof, meaning that even though not 100% comple-mentary, the inhibitors are capable of forming a duplex with SEQ ID NO: 1 by Watson-Crick type base pairing that is sufficient to inhibit or reduce neurodegeneration in vivo.

Accordingly, the present invention encompasses miR126-5p inhibitors having greater than about 70%, or greater than about 75%, or greater than about 80%, or greater than about 85%, or greater than about 90%, or greater than about 95%, or greater than about 99% of their nucleotides identical to those of SEQ ID NO: 4, or having greater than about 70%, or greater than about 75%, or greater than about 80%, or greater than about 85%, or greater than about 90%, or greater than about 95%, or greater than about 99% of their nucleotides that are complementary to SEQ ID NO:1.

In addition, the present invention also provides miR126-5p inhibitors that differ from those of SEQ ID NO:4 by only a certain number of nucleotides. For example, the present invention provides sequences that differ from SEQ ID NO:4 by no more than 10 nucleotides, or no more than 9 nucleo-tides, 8 nucleotides, 7 nucleotides, 6 nucleotides, 5 nucleo-tides, 4 nucleotides, 3 nucleotides, 2 nucleotides, or no more than 1 nucleotide. Similarly, the present invention provides miR126-5p inhibitors that are not 100% complementary to SEQ ID NOs: 1, but that contain mismatches at no more than 10 nucleotide positions, or more preferably no more than 9 positions, 8 positions, 7 positions, 6 positions, 5 positions, 4 positions, 3 positions, 2 positions, or more preferably no more than 1 nucleotide position.

One of skill in the art can readily produce such miR126-5p inhibitors using standard oligonucleotide synthesis and molecular biology methods, and can readily test such inhibi-tors to select those that are capable of forming a duplex with miR126-5p and/or that are capable of inhibiting the function and/or inhibiting neurodegeneration in vivo. The ability of a candidate miR126-5p inhibitor to form a duplex with miR126-5p should ideally be tested in vivo or at least inside cells. However, candidates can also be tested for their ability to form a duplex with miR126-5p in vitro, ideally using hybridization conditions selected to mimic those of the in-cyto environment.

By way of reference, "stringent hybridization conditions" are those that allow hybridization between two homologous nucleic acid sequences, but preclude hybridization of ran-dom sequences. Hybridization at high temperature and/or low ionic strength is termed "high stringency". In contrast, hybridization at low temperature and/or high ionic strength is termed "low stringency," which permits hybridization of less related sequences. Low stringency hybridization is generally performed at 0.15 M to 0.9 M NaCl at a tempera-ture range of 20° C. to 50° C. High stringency hybridization is generally performed at 0.02 M to 0.15 M NaCl at a temperature range of 50° C. to 70° C. Other factors that can affect stringency are the presence of formamide, tetrameth-ylammonium chloride and/or other solvents in the hybrid-ization mixture.

The nucleic acid-based inhibitors of miR126-5p of the present invention are preferably single-stranded, or substan-tially single-stranded antisense oligonucleotides, or at least have an active form within the cell that is single-stranded, or substantially single-stranded. However, the inhibitors may be double-stranded or partially double stranded or may comprise a hairpin structure. As used herein, partially double stranded refers to double stranded structures that contain fewer nucleotides in the complementary strand. In general, such partial double stranded agents will have less than 75% double stranded structure, or more preferably less than 50%, or more preferably less than 25%, 20% or 15% double stranded structure.

The nucleic acid based miR126-5p inhibitors of the invention may be of any length so long as they are capable of forming a duplex with miR126-5p as described above. For example, the nucleic acid based miR-126 inhibitors of the invention are around 12, 13, 14, 15, 16, 17, 18, 19, 20, 21, or 22 nucleotides in length. Furthermore, the nucleic acid-based miR126-5p inhibitors of the invention may be longer than 22 nucleotides in length and can comprise additional nucleotides at either end or internally in addition to those nucleotides that are complementary to miR126-5p. In preferred embodiments, the miR126-5p inhibitors are at least 19 nucleotides in length.

In preferred embodiments the miR126-5p inhibitors of the present invention (as well as the miR126-5p sequences of the invention) comprise nucleotides that have a desirable profile in terms of stability, nuclease resistance, hybridiza-tion thermodynamics, cell permeability, and sequence speci-ficity. The nucleic acid-based inhibitors of miR126-5p of the present invention can be made of ribonucleic acids, deoxy-ribonucleic acids, chemical variants or mimics of nucleic acids, or any combination thereof. Accordingly, the nucleic acid-based miR126-5p inhibitors of the present invention can comprise naturally occurring or non-naturally-occurring nucleobases, sugars, and covalent internucleoside (back-bone) linkages. The following paragraphs provide further details and examples of nucleotides that can be used in the nucleic acid-based miR126-5p inhibitors of the invention.

For example, the nucleic acid-based miR126-5p inhibitors of the present invention can comprise ribonucleotides, deoxyribonucleotides, 2'-modified nucleotides, phosphoro-thioate-linked deoxyribonucleotides, peptide nucleic acids (PNAs), locked nucleic acids (LNAs), ethylene nucleic acids (ENA), certain nucleobase modifications such as 2-amino- A, 2-thio (e.g., 2-thio-U), G-clamp modifications, antagomirs, nucleic acid aptamers, or any other type of modified nucleotide or nucleotide derivative that is capable of Watson-Crick type base pairing with a miRNA. For example, in addition to naturally occurring DNA and/or RNA nucleotide bases, non-naturally occurring modified nucleotide bases that can be used in the miR126-5p inhibitors of the invention include, but are not limited to, 8-oxo-guanine, 6-mercaptoguanine, 4-acetylcytidine, 5-(carboxyhydroxyethyl) uridine, 2'-O-methylcytidine, 5-carboxymethylamino-methyl-2-thioridine, 5-carb 1 pseudouridine, beta-D-galactosylqueosine, 2'-Omethylguanosine, inosine, N.sup.6-isopentenyladenosine, 1-methyladenosine, 1-methylpseudouridine, 1-methylguanosine, 1-methylaminomethyllinosine, 2,2-dimethylguanosine, 2-methyladenosine, 2-methylguanosine, 3-methylcytidine, 5-methylcytidine, N.sup.6-methyladenosine, 7-methylguanosine, 5-methylaminomethyluridine, 5-methoxyaminomethyl-2-thiouridine, beta-D-mannosylqueosine, 5-methoxycarbonyl-methyluridine, 5-methoxyuridine, 2-methylthio-N6-isopentenyladenosine, N-((9-beta-D-ribofuranosyl-2-methylthiopurine-6-yl) carbamoyl) threonine, N-((9-beta-D-ribofuranosylpurine-6-yl)N-methylcarbamoyl) threonine, uridine-5-oxyacetic acid methylester uridine-5-oxyacetic acid, wybutoxosine, pseudouridine, queosine, 2-thiocytidine, 5-methyl-2-thiouridine, 2-thiouridine, 2-thiouridine, 5-methyluridine, N-((9-beta-D-ribofuranosylpurine-6-yl) carbamoyl) threonine, 2'-O-methyl-5-methyluridine, 2'-O-methyluridine, wybutosine, and 3-(3-amino-3-carboxypropyl) uridine.

In other embodiments, the miR126-5p inhibitors of the present invention may include an aminoglycoside ligand, which may improve hybridization properties and/or sequence specificity. Exemplary aminoglycosides include, but are not limited to, glycosylated polylysine; galactosylated polylysine; neomycin B; tobramycin; kanamycin A; and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. In some embodiments, the guanidine analog (the guanidinoglycoside) of an aminoglycoside ligand is tethered to an oligonucleotide agent. In a guanidinoglycoside, the amine group on the amino acid is exchanged for a guanidine group. Attachment of a guanidine analog can enhance cell permeability of an oligonucleotide agent.

The miR126-5p inhibitors of the invention can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. A 3' conjugate, such as naproxen or ibuprofen, may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases.

The 5'-terminus can also be blocked with an aminoalkyl group, e.g., a 5'-O-alkylamino substituent. Other 5' conjugates can inhibit 5'-3' exonucleolytic cleavage. A 5' conjugate, such as naproxen or ibuprofen, may inhibit exonucleolytic cleavage by sterically blocking the exonuclease from binding to the 5' end of the oligonucleotide. Even small alkyl chains, aryl groups, or heterocyclic conjugates or modified sugars (D-ribose, deoxyribose, glucose etc.) can block 3'-5'-exonucleases.

The miR126-5p inhibitors of the present invention can also be attached to a peptide or a peptidomimetic ligand which may affect pharmacokinetic distribution of the miR126-5p inhibitor such as by enhancing cellular recognition, absorption and/or cell permeation. The peptide or peptidomimetic moiety can be about 5-50 amino acids long, e.g., about 5, 10, 15, 20, 25, 30, 35, 40, 45, or 50 amino acids long. A cell permeation peptide can also include a nuclear localization signal (NLS). Exemplary cell permeation peptides that may be conjugated to the miR126-5p inhibitors of the present invention are known in the art and include, but are not limited to, Penetratin, Tat fragment, Signal sequence based peptide, PVEC, and Transportan.

The peptide or peptidomimetic can be, for example, a cationic peptide, amphipathic peptide, or hydrophobic peptide (e.g., consisting primarily of Tyr, Trp or Phe). In another embodiment, the peptide moiety can include a hydrophobic membrane translocation sequence (MTS). The peptide moiety can be a "delivery" peptide, which can carry oligonucleotides across cell membranes. The peptide or peptidomimetic which may be tethered to the miR126-5p inhibitors of the invention may be a cell targeting peptide such as an arginine-glycine-aspartic acid (RGD)-peptide, or RGD mimic.

In other embodiments, the miR126-5p inhibitors of the invention may be attached to a cholesterol moiety, e.g., at the 3' or 5' end.

Inhibitors of miRNA function may be achieved by "antagomirs." Antagomirs are single-stranded, chemically-modified ribonucleotides that are at least partially complementary to the miRNA sequence. Antagomirs may comprise one or more modified nucleotides, such as 2'-O-methyl-sugar modifications. In some embodiments, antagomirs comprise only modified nucleotides. Antagomirs may also comprise one or more phosphorothioate linkages resulting in a partial or full phosphorothioate backbone.

The antagomirs may be at least about 75%, 80%, 85%, 90%, 95%, 96%, 97%, 98%, or 99% complementary to a mature miRNA sequence. In some embodiments, the antagomir may be substantially complementary to a mature miRNA sequence, that is at least about 95%, 96%, 97%, 98%, or 99% complementary to a target polynucleotide sequence. In other embodiments, the antagomirs are 100% complementary to the mature miRNA sequence.

The present invention contemplates methods for characterizing and testing known or potential candidates of miR126-5p inhibitors as well as methods of screening to identify new miR126-5p inhibitors. The characterization and screening assays of the present invention may be used to test for a variety of properties and/or activities of a miR126-5p inhibitor, including, but not limited to, binding to miR126-5p, decrease in expression of miR126-5p, degradation of miR126-5p, inhibition of activity of miR126-5p, inhibition of binding of miR126-5p to its target gene(s), alteration of expression of a miR126-5p target gene, effects on axonal degeneration, effects on a disease or condition of interest, such as neurodegeneration in ALS, and the like. There are many suitable screening methods known in the art which can be used in accordance with the present invention. For example, one of skill in the art can readily test for the ability of a candidate miR126-5p inhibitor to form a duplex with miR126-5p using any of the methods known in the art for testing duplex formation, such as various hybridization based assays, and the like.

For example, in one embodiment, the present invention can be used to screen miR126-5p inhibitors for their ability to treat NMD, or to prevent or delay the onset of NMD. Accordingly, in one aspect, the present invention provides for a method for determining whether a candidate miR126-5p inhibitor is capable of inhibiting miR126-5p in vivo in the spinal cord, the method comprising (a) administering a candidate miR126-5p inhibitor to the CNS, e.g., spinal cord, of an animal model of ALS disease; (b) measuring expression or activity of miR126-5p in the spinal cord of the animal, and (c) comparing the expression or activity of miR126-5p measured in the spinal cord to that in an ALS animal not injected with the candidate miR126-5p inhibitor or to that in an ALS animal which was injected with a control substance (such as the injection of a non-specific oligonucleotide), wherein a decrease in the expression of miR126-5p in the tested animal as compared to the non-treated animal indicates that the test compound may be a useful miR126-5p inhibitor. Multiple variations of the above screening method can be used. For example, one can compare the level of neurodegeneration in the control versus test animal, or compare the level of disease in the control versus test animal, or compare motor function or some other NMJ-related function in the control versus test subject. Techniques for observing and measuring neurodegeneration in a subject are within the skill in the art. Inhibition of neurodegeneration can also be inferred through observing a change or reversal in a pathogenic condition associated with the neurodegeneration. For example, improvement in the measurements of the CatWalk XT gait analysis may indicate an inhibition of neurodegeneration in the CNS/spinal cord. These and other variations in the screening methods described herein will be apparent to those of skill in the art.

Candidate compounds for testing can be obtained from various commercial sources or libraries of antisense oligonucleotides. Indeed, libraries of microRNA inhibitors are available from commercial sources.

Candidate miR126-5p inhibitors may include fragments or parts of naturally-occurring compounds or may be found as active combinations of known compounds which are otherwise inactive.

The nucleic acid based miR126-5p inhibitors of the invention can be synthesized in vitro by chemical synthesis using standard oligonucleotide synthesis methodology known to those of skill in the art. For example, the miR126-5p inhibitors of the present invention can be made using standard technology used to make synthetic oligonucleotides, such as methods that use phosphotriester, phosphite or phosphoramidite chemistry and solid phase techniques or via deoxynucleoside H-phosphonate intermediates.

Alternatively, the miR126-5p inhibitors of the invention can be expressed in a cell, for example by expression from an expression vector which comprises the nucleotide sequence encoding the miR126-5p inhibitor operably linked to a suitable promoter. The cell can be any desired cell. In a preferred embodiment, the cell is a glial cell. Methods of expressing nucleotide sequences in cells from expression vectors are well known in the art. For example, the expression vectors can be DNA plasmids or viral vectors. Oligonucleotide agent-expressing viral vectors can be constructed based on, but not limited to, lentivirus, adeno-associated virus, retrovirus, adenovirus, or alphavirus. In a preferred embodiment, the oligonucleotide agent-expressing viral vector is constructed based on lentivirus. Vectors for expression of miR126-5p inhibitors can be delivered to cells using any suitable transfection method, and may persist in, or stably integrate into the genome of, target cells. Alternatively, expression vectors may be used that provide for transient expression of the miR126-5p inhibitors of the invention. Such expression vectors can be repeatedly administered as necessary.

In certain embodiments, the nucleic acid-based inhibitor is operably linked to a promoter. In one embodiment, the promoter is a constitutively active promoter or an inducible promoter. In another embodiment, the promoter is a cell or tissue specific promoter. In still a further embodiment, the promoter is a glial cell specific promoter, such as GFAP promoter.

In certain embodiments of the invention, cells containing a nucleic acid construct of the present invention may be identified in vitro or in vivo by including a marker in the expression vector. Such markers can confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. Screenable markers such as GFP or luciferase can be used. The marker used is not believed to be important, so long as it is capable of being expressed simultaneously with the miR126-5p inhibitors of the invention. Further examples of selectable and screenable markers are well known to one of skill in the art.

It is to be understood that the sequence of miR126-5p has been highly conserved throughout evolution and is 100% conserved between humans, rats, dogs, chickens, zebrafish, and Fugu.

Pharmaceutical Compositions and Administration Routes

The pharmaceutical compositions of the present invention comprise an agent or an active agent as disclosed herein above, a pharmaceutically acceptable carrier, and optionally one or more excipients and auxiliaries.

The term "pharmaceutically acceptable" means approved by a regulatory agency of the Federal or a state government or listed in the U. S. Pharmacopeia or other generally recognized pharmacopeia for use in animals, and more particularly in humans.

Techniques for formulation and administration of active agents or drugs are well known in the art. The pharmaceutical compositions of the present invention can be manufactured by means of conventional mixing, dissolving, granulating, dragee-making, levigating, emulsifying, encapsulating, entrapping or lyophilizing processes.

The pharmaceutical compositions can be formulated for parenteral administration, e.g., for bolus injection or continuous infusion. Formulations for injection can be prepared in a unit dosage form, e.g., in ampoules, or in multidose containers, with optionally an added preservative. The compositions for parenteral administration can be formulated as suspensions, solutions or emulsions in aqueous or oily vehicles, and can contain excipients such as suspending, stabilizing and/or dispersing agents. For injection or infusion of an active agent, water is a preferred carrier. Saline solutions and aqueous dextrose and glycerol solutions can also be employed. Suitable oily or lipophilic vehicles or solvents include, but are not limited to, fatty oils, such as sesame oil, synthetic fatty acids esters, such as ethyl oleate, triglycerides, and liposomes.

Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the active ingredients to enable the preparation of highly concentrated solutions.

The active agent can be in a powder form for re-constitution with a suitable vehicle, e.g., sterile, pyrogen-free water based solution, before use.

The pharmaceutical compositions of the present invention can be administered locally or in a systemic manner.

According to some embodiments, the first pharmaceutical composition is administered via intramuscular or subcutaneous route of administration. According to a certain embodiment, the first pharmaceutical composition is administered by injection into a skeletal muscle tissue.

According to some embodiments, the second and third pharmaceutical compositions of the present invention are formulated to penetrate the blood brain barrier to reach the CNS.

According to additional embodiments, the second and third pharmaceutical compositions of the present invention circumvent the blood-brain barrier (BBB) and are delivered directly to the spinal cord or CNS. The second and third pharmaceutical compositions can be delivered directly into the CNS by transport along a neural pathway to the CNS, or by way of a perivascular channel, a prelymphatic channel, or a lymphatic channel associated with the brain and/or spinal cord. The second and third pharmaceutical compositions can deliver the agent to the cerebrospinal fluid and then subsequently to the CNS, e.g., to the brain, and/or spinal cord.

Conventional approaches for drug delivery to the central nervous system (CNS) include: neurosurgical strategies (e.g., intrathecal, intracerebral or intracerebroventricular injection or infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

According to some embodiments, the second and third pharmaceutical compositions are delivered to the spinal cord or CNS by injection or infusion. Thus, the second and third pharmaceutical compositions can be administered via the spinal route (into the cerebrospinal fluid (CSF)), or via intrathecal or intraventricular route of administration.

Alternatively, the pharmaceutical compositions of the present invention can be delivered by any known route of administration including, but not limited to, intravenous, intra-arterial, subcutaneous, oral, transdermal, nasal, and rectal administration routes.

According to some embodiments, the first, second and/or third compositions can be combined to form a single combination composition. Thus, according to additional embodiments, the first and second or the second and third pharmaceutical compositions are combined to form a single composition. According to additional embodiments, the first, second and third pharmaceutical compositions are combined to form a single composition.

The pharmaceutical compositions comprise a therapeutically effective amount of the active agents so as to achieve the intended purpose. The term "therapeutically effective amount" means an amount of the active agent effective to treat, alleviate or ameliorate a MND (e.g., ALS) or a NMJ abnormality or one or more symptoms associated therewith or prolong the survival of the subject being treated.

Toxicity and therapeutic efficacy of the active agents described herein can be determined by standard pharmaceutical procedures in vitro, in cell cultures or in experimental animals. The data obtained from these in vitro cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition.

Depending on the severity of the condition to be treated, dosing can be of a single or a plurality of administrations, with course of treatment lasting from several days to several months or until cure is achieved or diminution of the disease state or symptoms thereof is obtained.

In determining the dosages of the agents to be administered, the dosage and frequency of administration can be selected in relation to the pharmacological properties of the nucleic acids to be delivered (i.e., naked RNA, vectors, delivery particles used, and the like). According to some embodiments, the miR molecules or the expression vectors (alone or in combination with other agents) can be administered in a dose of between about 0.01 mg and about 10 mg per administration/treatment per day. For example, the amount can be between about 0.01 mg and about 8 mg per administration/treatment or between about 0.01 mg and about 2 mg per administration/treatment. In some embodiments, the doses disclosed herein can be administered at any administration regime, such as, once a day; once a week, once a month, and the like, or at interval so as to achieve treatment of the disease or reduce or inhibit the one or more symptoms thereof.

It will be appreciated that the active agents of the invention can be administered alone or in conjunction with other known therapeutic agents. Thus, for example, the miRNAs of the present invention can be administered together with any anti-MND agent (e.g. anti-ALS agent) capable of attenuating NMD progression or NMJ abnormality progression.

Motor Neuron Diseases and Neuromuscular Junction Abnormalities

The present invention provides methods of treating motor neuron diseases (MNDs) and neuromuscular junction (NMJ) abnormalities.

Motor neuron diseases include, but are not limited to, Amyotrophic Lateral Sclerosis (ALS), also known as Lou Gehrig's Disease, primary lateral sclerosis, progressive muscular atrophy, pseudobulbar palsy, progressive bulbar palsy, lower motor neuron disease, Spinal Muscular Atrophy type 1 (SMA1, Werdnig-Hoffmann Disease), Spinal Muscular Atrophy Type 2 (SMA2), Spinal Muscular Atrophy Type 3 (SMAS, Kugelberg-Welander Disease), and Charcot-Marie-Tooth Disorders.

Additional diseases affecting motor neurons include, but are not limited to, Kennedy disease, post-polio syndrome, hereditary spastic paraplegia (HSP), Gareis-Mason syndrome, Allan-Herndon-Dudley syndrome, Troyer syndrome, Lison syndrome, spastic ataxia, and SPOAN syndrome.

According to one embodiment, the motor neuron disease (MND) is Amyotrophic Lateral Sclerosis (ALS).

According to additional embodiments, the ALS is familial (inherited) ALS or sporadic ALS.

ALS is a progressive neurodegenerative disease that destroys nerve cells and causes disability. ALS often begins with muscle twitching and weakness in a limb, or slurred speech. It affects control of the muscles needed to move, speak, eat and breathe. There is no cure for ALS and the disease is fatal. Early signs and symptoms of ALS include: difficulty in walking or doing normal daily activities; tripping and falling; weakness in legs, feet or ankles; hand weakness or clumsiness; slurred speech or difficulty in swallowing; Muscle cramps and twitching in the arms, shoulders and tongue; difficulty in holding the head up or keeping good posture.

Once a subject is diagnosed as having MND or NMJ abnormality, the active agent according to the principles of the present invention, e.g., miR126-5p, a precursor thereof, a seed or homolog thereof; a polynucleotide sequence encoding same, or an expression vector comprising the polynucleotide is administered to the subject. According to the present invention, increasing miR126-5p expression or up-regulation of miR126-5p in certain cells, e.g., skeletal muscle cells and/or motor neurons, is regarded as an increase by at least 10%, 20%, 30%, 40%, 50%, 60%, 70%, 80%, 90% or more, alternatively by at least 2 fold or more, of the levels or activity of miR126-5p in treated skeletal muscle cells or tissue and/or motor neurons as compared to the levels or activity of miR126-5p in non-treated skeletal muscle cells or tissue and/or motor neurons. The level and activity of miR126-5p in skeletal muscle cells or motor neurons can be evaluated by methods known in the art or by the methods disclosed in the examples herein below, for example, by evaluating one or more symptoms of the disease, e.g., improvement in walking, reduction in hand weakness, improvement in speech, and the like. Additionally, inhibiting miR126-5p expression in certain cells, e.g., glial cells, is regarded as a decrease by at least 10%, 20%, 30%, 40%, 50%, 60%, 70%, 80%, 90% or more, alternatively by at least 2 fold or more, of the levels or activity of miR126-5p in glial cells as compared to the levels or activity of miR126-5p in non-treated glial cells. The level and activity of miR126-5p in glial cells can be evaluated by methods known in the art or by the methods disclosed in the examples herein below, for example, evaluating one or more symptoms of the disease, e.g., improvement in walking, reduction in hand weakness, improvement in speech, and the like.

Neuromuscular junction abnormalities include, but are not limited to, myasthenia gravis, Lambert-Eaton myasthenic syndrome, muscular atrophy, and peripheral nerve injuries.

According to some embodiments of the present invention, the subject can be administered with a nucleic acid-based inhibitor capable of down-regulating an activity or expression of miR126-5p.

The compositions and methods of the invention are used to inhibit neurodegeneration of motor neurons and disruption of NMJ in humans.

In addition to treating pre-existing conditions, the compositions of the present invention can also be administered prophylactically in order to prevent or slow the onset of the MND or NMJ abnormality or to attenuate the progression of the MND or NMJ abnormality.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Animals and Vector Injections

HB9::GFP (Stock No: 005029) mice were originally obtained from Jackson Laboratories. The colony was maintained by breeding with ICR mice. SOD1$^{G93A}$ (Stock No: 002726) mice were originally obtained from Jackson Laboratories and maintained by breeding with C57BL/6J mice. Genotyping was performed using the polymerase chain reaction (KAPA® Bio systems); DNA samples were generated from ear or tail tissue biopsies. All injection procedures were performed on pre-symptomatic ~P60 mice. Mice were first anesthetized using a mixture of Xylasin and ketamine. Next, 100 μL of Neurobasal® containing ×10 concentrated *lenti*-viruses (6×10$^9$ titer units), were injected into the gastrocnemius (GC) muscles using a 1 ml syringe and a 25G needle. A pLL-miR126-5p-GFP construct was injected into the right hind foot, whereas a pLL-miR142-GFP construct was injected into the left hind foot. All animal experimentations were approved by the Tel-Aviv University Animal Ethics Committee.

Microfluidic Chamber Preparation

Polydimethylsiloxane (PDMS) microfluidic chambers (MFC) were designed and cast as described previously (Ionescu et al., 2016). After the wells were punched, a small 'cave' was created in the explant well near the grooves using a 25G needle, keeping the explant in place. Microfluidic devices were cleaned of surface particles using adhesive tape and were sterilized in 70% ethanol for 15 minutes. Devices were completely dried under sterile conditions using UV radiation, and then attached to a sterile 60-mm plastic dish (Nunc) with gentle pressure, and the margins were sealed with PDMS before incubation at 70° C. for 30 minutes to prevent the detachment of the chamber. Muscle channels were coated with Matrigelx diluted 1:10 with DMEM containing 2.5% penicillin-streptomycin-nystatin (PSN) for 30 minutes at 37° C., before filling the muscle wells with 150 μL of Bioamf-2 medium. The explant well and channel were filled with 150 μL of 1.5 ng/mL poly-D-L-ornithine (PLO, Sigma) in PBS overnight, and then replaced with 150 μL laminin (Sigma), 1:333 in deionized distilled water (DDW) overnight. One day before plating the spinal cord explant, laminin was replaced with explant medium containing Neurobasal® (Life Technologies) supplemented with 2% B27 (Invitrogen), 1% penicillin-streptomycin (Biological Industries), 1% Glutamaxx (Life Technologies), 25 ng/mL brain-derived neurotrophic factor (Alomone Labs), until the day on which co-culturing began.

Fluorescence Microscopy and Image Analysis

All confocal images were captured using a Nikon Ti microscope equipped with a Yokogawa CSU X-1 spinning disc and an Andor iXon897 EMCCD camera controlled by Andor IQ2 software. Epifluorescence was imaged using the same microscope in Bright field mode and images were captured with an Andor Neo sCMOS camera, or at a FLoid benchtop imaging station (Life Technologies). TIRF images were captured using a TILL photonics iMIC microscope (FEI Munich GmbH) with an Andor iXon897 EMCCD camera. All live-imaging assays were performed in a humidified 5% CO2 incubation chamber.

Western Blotting

Muscle and sciatic nerve tissues of both sexes were excised and homogenized in lysis buffer containing PBS, 1% Triton X-100® (Sigma), and 1× protease inhibitors (Roche), followed by centrifugation and collection of the supernatant. Protein concentration was determined using the Bio-Rad Protein Assay. Protein samples were denatured by boiling in SDS sample buffer, which were then electrophoresed in 10% polyacrylamide gels (SDS-PAGE). Proteins were transferred to a nitrocellulose membrane and then immunoblotted with appropriate primary antibodies: Sema3A (Abcam; 1:1000); NRP1 (Abcam; 1:1,000); Sema3B (Abcam; 1:2000); NRP2 (Cell signaling, 1:1000) GFP (Abcam, 1:5000), Tubulin (1:10,000), and ERK (1:10,000), diluted in 5% (w/v) Skim-milk (BD Difco) in TBS-T, followed by species-specific HRP-conjugated secondary antibodies (Jackson Laboratories 1:10000) and visualized using a myECL imager (Thermo), according to the manufacturer's instructions. Quantification was performed using ImageJ software.

Isolation and Culture of hMSC

Human mesenchymal stem cells (hMSC) from healthy donors and ALS patients used in this study were obtained from bone marrow samples and were isolated, and then phenotypically characterized and cultured as described previously (Nachmany et al., 2012). All volunteers in this work signed a consent form before sample donation, according to the guidelines of the Hospital's Ethics Committee supervised by the Israeli Health Ministry Ethics Committee conforming with The Code of Ethics of the World Medical Association (Declaration of Helsinki), printed in the British Medical Journal (Jul. 18, 1964).

Motor Neuron Cell Culture

Primary spinal cord neurons were cultured using E12.5 mouse embryos of either sex. Briefly, spinal cords were excised, trypsinized, and triturated. Supernatant was collected and centrifuged through a 4% BSA cushion. The pellet was re-suspended and centrifuged through an Optiprep® gradient (10.4% Optiprep® (Sigma-Aldrich), 10 mM Tricine, 4% glucose) for 20 min at 760×g with the brake turned off. Cells were collected from the interface, washed once in complete medium, and then plated in coated growth chambers. Cells were maintained in Complete Neurobasal® Medium (Gibco) containing B27 (Gibco), 10% (v/v) horse serum (Biological Industries), 25 nM beta-mercaptoethanol, 1% Penicillin-Streptomycin (PS; Biological Industries), and 1% GlutaMAX® (Gibco) supplemented with 1 ng/mL Glial-Derived Neurotrophic Factor (GDNF), 0.5 ng/ml Ciliary Neurotrophic Factor (CNTF), and 1 ng/ml Brain-Derived Neurotrophic Factor (BDNF), (Alomone Labs). Prior to plating, the growth plates were coated with 1.5 g/mL poly D-L-ornithine (PLO; Sigma-Aldrich) overnight at 37° C. and 3 g/mL Laminin (Sigma-Aldrich) for 2 hours at 37° C. For immunofluorescence staining, 30,000 cells were plated on cover slides in 24-well plates. Cells were grown at 37° C. in 5% $CO_2$.

Spinal Cord Explants

Spinal cords were dissected from E11.5 mouse embryos of both sexes, either using HB9::GFP or SOD1$^{G93A}$ stripped of meninges and dorsal root ganglia. The ventral horn was separated from the dorsal horn by longitudinal cuts along the spinal cord, and transverse sections up to 1 mm were placed in the explant well. Prior to plating, the growth chambers were coated with 1.5 g/mL PLO overnight at 37° C. and 3 g/mL Laminin overnight at 37° C. Explants were maintained in Spinal Cord Explant Medium containing NeurobasalR, 2% B27, 1% PS, and 1% GlutaMAX®, supplemented with 25 ng/mL BDNF. Explants were grown at 37° C. in 5% $CO_2$.

Primary Myocyte Culture

Skeletal muscle cultures were derived from the gastrocnemius (GC) muscle of adult P60 female mice of either SOD1$^{G93A}$ background or their littermates (LM). Briefly, gastrocnemius (GC) muscles were excised and incubated in 2 mg/mL collagenase I (Sigma-Aldrich) in DMEM containing 2.5% penicillin-streptomycin-nystatin (PSN, Biological Industries) for 3 hours. Muscles were then dissociated and incubated for 3 days in Matrigel®-coated (BD Biosciences) six-well plates with Bioamf-2 medium (Biological Industries) with 1% PSN at a density of ~120 myofibers per well. For purification of the myoblasts, adherent cells were trypsinized and pre-plated in an uncoated dish for 1 hr at 37° C. Non-adherent cells were then transferred into a Matrigel®-coated dish with Bioamf-2 medium. Pre-plating was repeated for two days, keeping the culture at less than 50% confluence, before plating cells in MFC. Cultures were maintained at 37° C. and in 5% $CO_2$. After the final pre-plating, 100,000 myocytes were cultured in the pre-coated distal compartment of the MFC. Myocyte Conditioned Media (CM) were produced as follows: At the final pre-plating stage, myoblasts were cultured in a Matrigel®-coated 100 mm dish at 80% confluence and were incubated for 2 days with Bioamf-2 medium, followed by 2 days with rich DMEM (Biological Industries) medium containing 10% Fetal Calf Serum (Biological Industries), 10% Horse Serum (Biological Industries), 1% GlutaMAX®, and 1% PSN. Then, once muscles reached a fully differentiated state, the culture dish was rinsed 3 times with pre-heated PBS and poor DMEM medium containing 1% GlutaMAXR and 1% PSN was applied on the cultures. CM was collected after 2 days, centrifuged for 5 minutes at 400×g at 25° C., and streamed through a 0.22 μm PES filter.

CM Preparation and Application

Muscle myocytes of WT or SOD1$^{G93A}$ mice were cultured as described (Ionescu et al., 2016). Seven days after myocytes were fully differentiated, the muscles kept growing for 3 days in complete Neurobasal® containing BDNF and GDNF. The conditioned media was refreshed with BDNF, GDNF, and Glucose after its collection. Conditioned media under both conditions was applied on the axon compartment of the MFC for 48 hr.

Lentiviral Vectors

Genes of interest were cloned into a third-generation lentiviral pLL3.7 backbone. HEK293T cells were transfected by employing calcium phosphate method and a mixture consisting of the vector of interest, vesicular stomatitis virus glycoprotein, and group antigens-polymerase (reverse transcriptase) was used. The medium was replaced after 5-8 hours, and the supernatant was collected 48 hours later. Next, 50 mM Hepes were added before freezing to maintain a neutral pH for long-term storage. When necessary, lentiviruses were concentrated using a PEG Virus Precipitation Kit (Abcam).

Neuromuscular Junction Staining

GC was excised from P60 mice and cleared of connective tissue, washed in PBS, fixed in 4% paraformaldehyde, washed once more, and then incubated with 1 g/mL Rhodamine Red-Conjugated Bungarotoxin (Sigma-Aldrich). Tissues were washed and then treated with methanol at −20° C. for 5 min, washed, and then blocked in blocking solution for 1 hour. Tissues were then rocked with appropriate primary antibodies diluted in blocking solution at room temperature overnight. Antibodies were used at the following concentrations: anti-Neurofilament Heavy Chain 1:500 (Abcam; 1:1000; NFH) Synaptophysin (Millipore, 1:300) Synaptotagmin (Alomone ant-003 1:300); anti-NRP1 1:100; anti-Sema3A 1:100; anti-NRP2 1:100; anti-Sema3B 1:100. After washing, secondary antibodies (DyLight 405 anti-chicken 1:500; AlexaFluor 488 anti-chicken 1:500; AlexaFluor 647 anti-rabbit 1:500) were added for 4 hours at room temperature. Muscle fibers were spread into monolayers under a stereomicroscope and affixed to slides using VectaShield® (Vector Laboratories). Cover slides were sealed with clear nail polish.

Quantification of Myocyte Contraction 1,000-frame-long movies of myocytes in the distal compartment of the microfluidic chamber were acquired 7 days post co-culturing. Imaging was performed under bright-field conditions at a rate of ~33 fps while using a 20× objective. A myocyte contraction plot was then profiled using an image-based method. Briefly, only myocytes that came in contact with axons were plotted. Time-lapse images were taken for analysis using ImageJ. To create a time trace of contractions, high contrast (bright or dark) regions of interest (ROIs) were selected on each myotube. Movement of the selected spot due to myotube contraction was assessed by the change in the ROI intensity over time. The number of strong contractions, as measured from the time trace, was manually validated by re-examining the time-lapse image series. The number of strong and weak contractions in innervated myotubes was compared before and after 1 µM TTX was added to the neuronal compartment. A myotube with a post to pre TTX difference of >50% was measured as an increase or decrease in contraction, and the fraction of increased, decreased, and unchanged myotubes was calculated.

Immunostaining of Cell Cultures

Cultures were fixed in 4% paraformaldehyde and permeabilized with 0.1% Triton X-100*, 5% DS, 1 mg/mL BSA in PBS. Samples were blocked for 1 hour with blocking medium containing 5% DS, 1 mg/mL BSA in PBS. Primary antibodies against NFH (1:500), NRP1 (1:100), Sema3A (1:100), NRP2 (1:100), Sema3B (1:100), and Acetylated RNA Extraction and cDNA Synthesis Muscle tissues were immediately frozen with liquid nitrogen. Tissue was ground to powder using a pestle and mortar. Then 700 µL of TriReagent (Sigma-Aldrich) were added to the muscle powder and the samples were further passed through a 21G needle 3 times for better homogenization. RNA from the TriReagent-rinsed samples was further isolated following the TriReagent protocol. RNA quality was measured using NanoDrop3000 and a bio-analyzer. RNA purification of MN mass culture, along with transfected Hela cells, was performed using TriReagent protocol as well. mRNAs were pooled in equal amounts and reverse transcribed into double-stranded cDNA by using the SuperScript2® kit (Qiagene).

NanoString® Chip

One-hundred ng RNA samples were outsourced to NanoString® technologies' facilities for a miR-Chip array assay of ~800 known miRs (Nanostring Technologies, Inc.). miR was quantified automatically by NanoString® Technologies' instrumentation for miRs, which was hybridized with the template. Output data were analyzed by the nCounter analysis system. All miRs were normalized to the 100 most abundant miRs in the samples.

Primers Design

Based on the consensus sequences of the desired transcripts, 2 sets of primers were designed for each gene (h—Human gene; m—Murine gene).

| Gene | Forward Primer | Reverse Primer |
|---|---|---|
| hHPRT | GAACCAGGTTATGACCTTGATTTAT<br>SEQ ID NO: 5 | GCAAGACGTTCAGTCCTGT<br>SEQ ID NO: 6 |
| hSema3A | GCTCCAGTTATCATACCTTCCTTTTG<br>SEQ ID NO: 7 | ACTGGCCACACAATCTTTTGAA<br>SEQ ID NO: 8 |
| hNRP1 | ACCTGTTCTCTTTCAGGGAA<br>SEQ ID NO: 9 | CAAGTTGCAGGCTTGATTCG<br>SEQ ID NO: 10 |
| hB2M | CCGTGTGAACCATGTGACTT<br>SEQ ID NO: 11 | GGCATCTTCAAACCTCCATGA<br>SEQ ID NO: 12 |
| hNRP2 | GAGGCCAACCAGACCCA<br>SEQ ID NO: 13 | CGTAAACAATCCACTCGCAGTT<br>SEQ ID NO: 14 |
| hSema3B | TCTCCTTCCAAGTCCA<br>SEQ ID NO: 15 | CTCGGCACCCACAAACA<br>SEQ ID NO: 16 |
| mSema3A | CACTGGGATTGCCTGTCTT<br>SEQ ID NO: 17 | GGCCAAGCCATTAAAAGTGA<br>SEQ ID NO: 18 |
| mGFP | GCTACCCCGACCACATGAAGCA<br>SEQ ID NO: 19 | GTCTTGTAGGTGCCGTCGTCCTTG<br>SEQ ID NO: 20 |
| m-miR126 | GTGTGGCTGTTAGGCATGGT<br>ID000451 (Thermo Fisher Scientific)<br>SEQ ID NO: 21 | CATTGCACTGTCCACTCCTG<br>ID000451 (Thermo Fisher Scientific)<br>SEQ ID NO: 22 | tubulin (1:1000), Ryanodine receptor 1 (Millipore, 1:500), Alpha Actinin (Sigma, 1:400) Tau5 (Abcam, 1:500) MAP2 (Millipore, 1:500) were diluted in blocking solution and incubated overnight at 4° C. Samples were incubated with species-specific fluorescent secondary antibodies for 2 hours at room temperature. DAPI was used for visualizing nuclei in myotubes. In MFC, after the staining protocol was completed, the MFC was peeled from the dish by gently pulling it from the proximal to the distal side. ProLong mounting medium was added and samples were covered with a #1.5, 18×18 mm cover-slide.

qPCR for mRNA Detection

Quantitative Polymerase Chain Reaction (qPCR) was performed on the StepOne system (Life Technologies) in a 10 µL reaction containing 4 µL of RNA (20 ng), 5 µL Syber® green master mix (Thermo Fisher Scientific), and 1 µL of reverse and forward primers.

miR Vectors and Transfection

Mammalian expression vector pMSCV-Blast-miR constructs were generously provided by Eran Hornstein from the Weizmann Institute of Science. Mammalian expression vector of C9orft72 Di-peptide $PR_{50}$ and $GR_{50}$ constructs were generously provided by David Trotti from Jefferson University (Wen et al., 2014). Next, 50,000 HeLa/U87 human glioblastoma/muscles 4924-7371-4247\2 cells were plated in rich DMEM medium (1% PS, 1% GlutaMAX®, 20% FBS). After 24 hours, the culture medium was replaced with serum-free medium (Opti-MEM®) and cells were transfected using FuGene NE 6 (Promega) protocol. Cells were collected after 48 hours and used either for a functional assay or for RNA/protein extracts. Myocyte cultures were transfected using the same approach.

Semaphorin Preparation

HEK293T cells were stably transfected to overexpress either Sema3A or an empty control. Conditioned media from 80% confluent cultures were collected after 3 days. We validated the purity level of the collected media using Coomassie staining and identified the stained band with a specific antibody against the desired protein using western blot analysis.

NRP1 Antibody Application

Five µg/ml NRP1 antibody (R&D System) for the extracellular domain was added to the distal compartment of the MFC while maintaining a proximal-to-distal volume gradient.

Histology Tissue Collection & Fixation

Gastrocnemius muscles of 20 samples were harvested and fixed in 4% PFA. The samples were then outsourced for a histological assessment at Patho-Logica Company, Ness-Ziona, Israel. All tissues were trimmed into block cassettes and sent to CDX-Diagnostics for slide preparation.

Slide Preparation & Histological Evaluation

Tissues were trimmed, embedded in paraffin sections at no more than 5 µm thickness and stained with Hematoxylin & Eosin (H&E). The mean minimal muscle fiber diameter thickness was measured in microns by performing a manual count using a 10× lens and analyzed by expert pathologist.

xCELLigence® impedance measurement

For each experiment, 30,000 U87 cells were plated with rich DMEM medium in E-Plate L8 wells and incubated together with the xCELLigence® system (ACEA Biosciences, Inc.) at 37° C., 5% $CO_2$ overnight. Impedance data were collected at 5-minute intervals. After 24 hours, poor DMEM medium (1% PS, 1% GlutaMAX®) with Sema3A or its control medium was replaced and recording proceeded. The data was analyzed using RTCA data analysis software 1.0 and normalized to the control sample.

CatWalk XT Gait Analysis

The Catwalk is a video-based analysis system used to assess gait in voluntarily walking mice (Noldus information technology). The principle of this method is based on an optical technique. The light of a fluorescence tube is completely internally reflected on a glass walkway floor. When the animal crosses the walkway, the light leaves the glass and illuminates only the area of contact. In this way, the different paw contacts are visualized. Based on position, pressure, and the surface area of each foot paw multiple parameters are calculated. Only compliant and continuing trials for each animal were analyzed, averaged, and the mean was calculated.

Experimental Design and Statistical Analysis

Data is expressed as mean±SEM. The statistical analysis was assessed by Student's t-test. In all cases, differences were considered to be statistically significant if $p < 0.05$. Symbols are as follows: *: $P < 0.05$, : $P < 0.001$, *: $P < 0.0001$.

Example 1

Figure 1B:
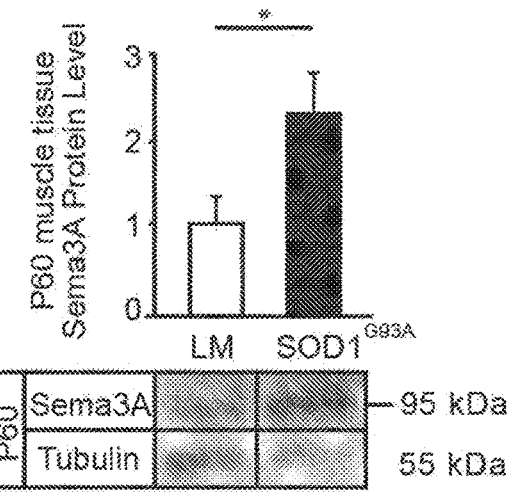
Figure 1C:
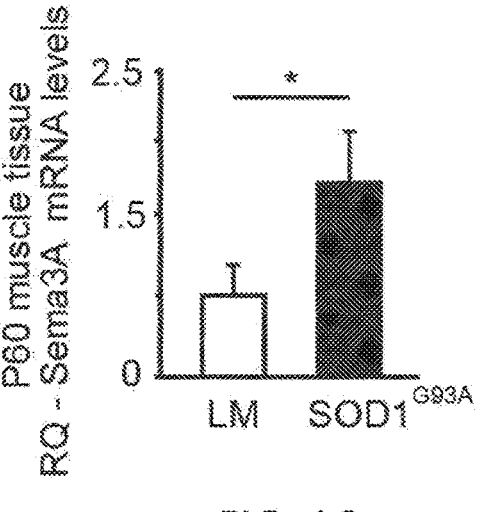

Sema3A and NRP1 Levels are Elevated in Muscles and in Motor Neurons of ALS Models Sema3A is known to be a destabilizing factor, at least in development, and it was previously shown that Sema3A is elevated in ALS. In order to evaluate the effect of Sema3A secreted from ALS mutant muscles on axon degeneration of motor neurons (MNs), the expression of Sema3A in SOD1$^{G93A}$ gastrocnemius (GC) muscles in comparison with that of their littermates (LM) was first examined. Western blot analysis of muscle protein extracts revealed significant elevations in Sema3A protein levels in muscles of pre-symptomatic SOD1$^{G93A}$ mice as early as P30 and P60 (FIGS. 1A-B), while the levels of Sema3A in younger animals (P7) showed no apparent differences compared with their LM controls. In order to validate this difference, the transcript levels of Sema3A were measured (FIG. 1C). Quantitative PCR analysis of total RNA extracts from muscles at pre-symptomatic SOD1$^{G93A}$ stage and LM mice identified a ~1.7-fold increase in Sema3 A mRNA in SOD1$^{G93A}$ muscles.

Figure 1D:
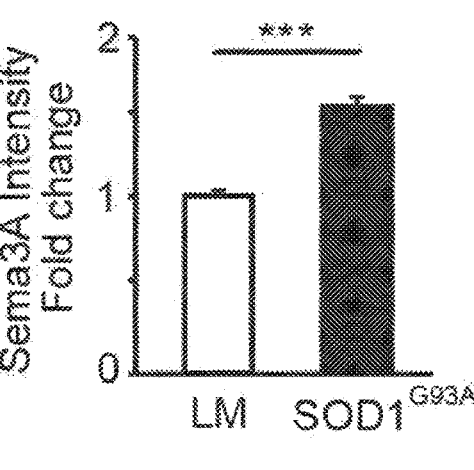

Since GC muscle tissues contain heterogeneous cell types, and in order to verify that the levels of Sema3A were indeed higher specifically in SOD1$^{G93A}$ muscles fibers, primary myocyte cultures from P60 SOD1$^{G93A}$ and LM mice were immunostained for Sema3A. Quantifying the mean intensity values showed a significant increase of 50% in the SOD1$^{G93A}$ myocytes (FIG. 1D).

Figure 1E:
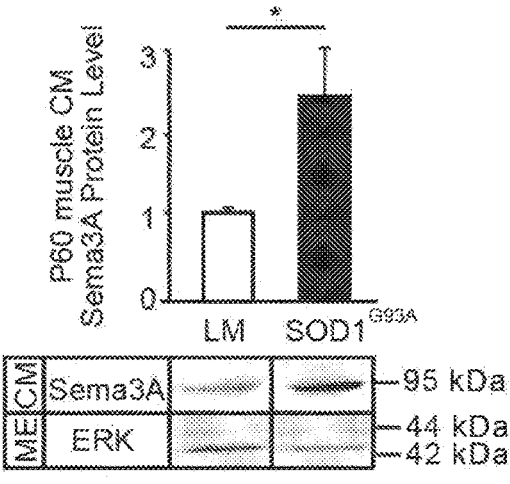

Conditioned media (CM) was also collected from myocyte cultures to determine whether the increase in Sema3A protein also resulted in an increase in its secretion. Western blot analysis indicated that Sema3A levels were also elevated in P60 SOD1$^{G93A}$ myocyte-conditioned media (FIG. 1E).

Figure 1F:
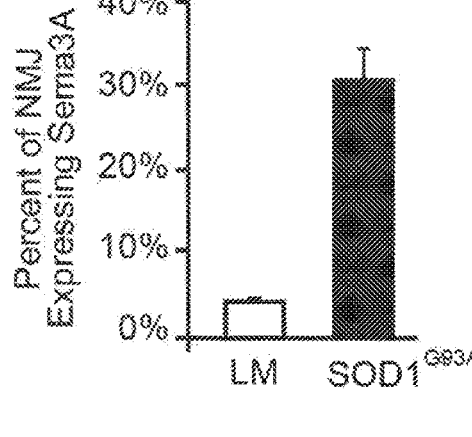

Because neuromuscular junction (NMJ) disruption is a primary event in ALS, levels of Sema3A in NMJ in vivo were examined. Immunostaining for Sema3A in GC muscles showed a 6-fold increase in the number of muscle fibers expressing Sema3 A in their NMJs. Whereas only ~5% of NMJs stained positively for Sema3A in LM muscles, Sema3A expression in NMJs in P60 SOD1$^{G93A}$ mice reached a level of ~30% (FIG. 1F).

Previous study described Sema3A elevation in SOD$^{G93A}$ mice, specifically in fast fatigue NMJs expressing myosin-IIb marker. Since fast fatigue NMJs are the first to become disrupted and be eliminated in ALS pathology, the inventors of the present invention examined Sema3A levels both at P90 and P120 of ALS mutant mice. Whereas the percentage of NMJs expressing Sema3A in SOD$^{G93A}$ mice at P90 was similar to P60, the end stage animals (P120) were shown to display a reduction in Sema3A-positive NMJs and no apparent difference existed between WT and SOD1$^{G93A}$ mice. Taken together, these results indicated that a significant part of the MN population is exposed to high levels of Sema3A in pre-symptomatic stages and that this specific population is disrupted and eliminated during disease progression.

Figure 1G:
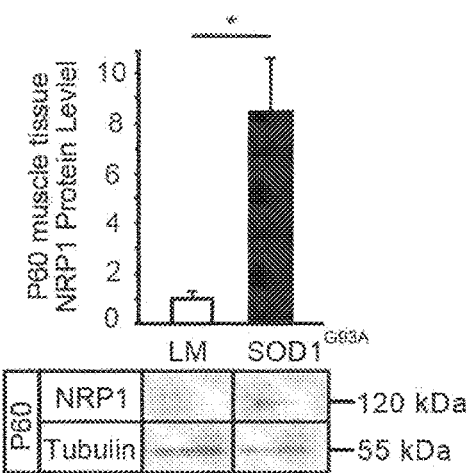
Figure 1H:
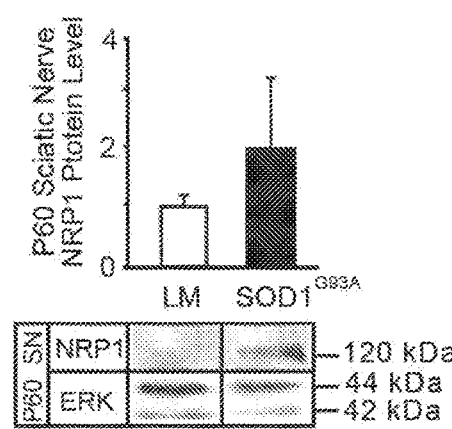
Figure 1I:
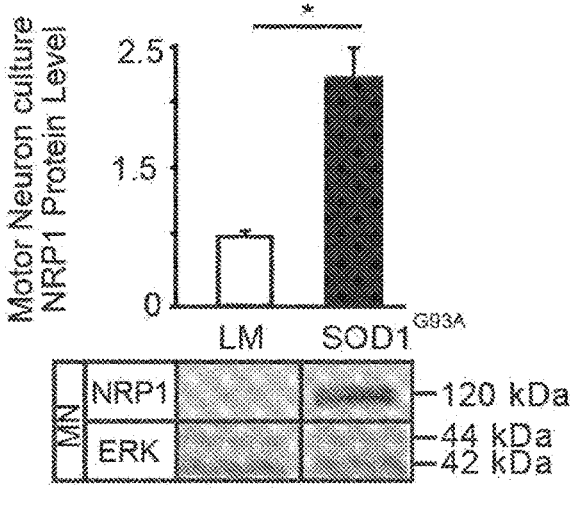
Figure 1J:
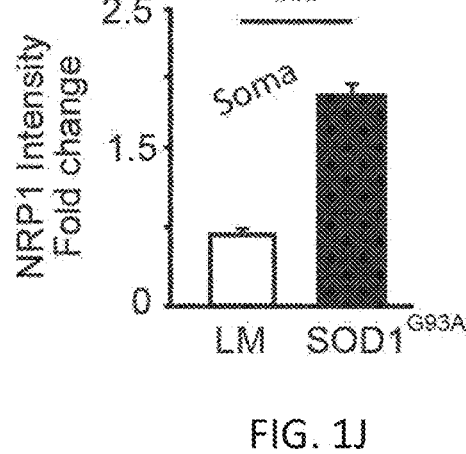
Figure 1K:
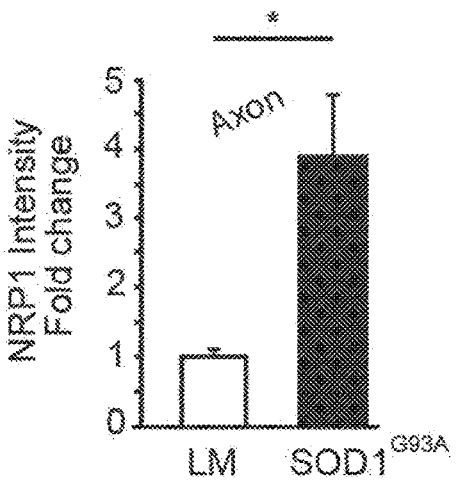
Figure 1L:
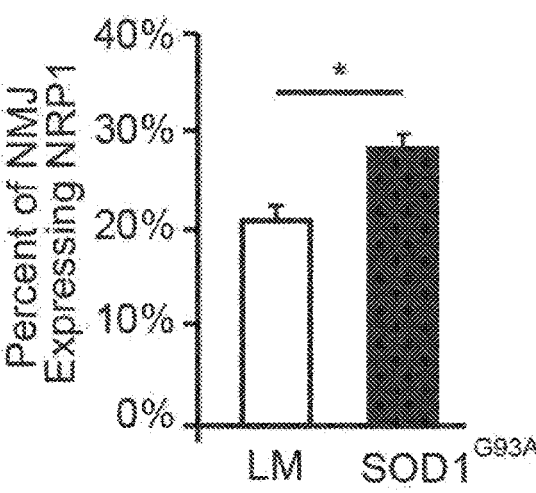

Next, the expression of Sema3A-receptor binding unit, NRP1, in ALS was evaluated. Western blot analysis of NRP1 in GC muscle extracts of SOD1$^{G93A}$ ALS mice revealed a significant ~8-fold increase compared to the level in GC muscle extracts of LM (FIG. 1G). Since MNs are a primary target in ALS, the possibility that NRP1 is also overexpressed in the MNs of ALS mutant mice was next examined. Western blot analysis of sciatic nerves (SNs) was performed, showing a ~2-fold elevation in NRP1 levels of P60 SOD1$^{G93A}$ mice (FIG. 1H). Next, protein extracts of primary MN cultures were obtained for western blot analysis and confirmed a ~2.5-fold elevation in NRP1 levels in the MNs of SOD1$^{G93A}$ culture (FIG. 1I). Quantification of primary MN cultures immunostained for NRP1 resulted in analogous findings (FIGS. 1J-K). Intriguingly, the NRP1 signal in SOD1$^{G93A}$ was generally higher than in LM, and was increased even more in axons (FIG. 1K) compared with cell bodies (FIG. 1J). Finally, quantification of immunostaining for NRP1 in GC muscles confirmed a similar shift of ~30% in the number of NMJs expressing NRP1, as observed for Sema3A in SOD1$^{G93A}$ mice, both at P60 (FIG. 1L) and P90. However, also this time, the differences were abolished in the end stages of the disease (P120).

In order to determine whether the elevated NRP1 levels resulted from feedback due to an increase in its ligand, primary MN cultures from LM embryos were treated with soluble Sema3A for 3 days and western blot analysis was performed on cell culture lysates. Importantly, no difference was observed in NRP1 expression after applying Sema3A, suggesting that NRP1 levels are regulated by an intrinsic mechanism in MNs. Finally, to confirm the finding of the impact of Sema3A in ALS, western blot analysis for Sema3A and NRP1 expression in human mesenchymal stem cells from sporadic ALS patients and healthy controls was performed, as well as in myocyte-expressing C9orf72-PR$_{50}$ and their conditioned media for Sema3A. In addition, the results were compared with those of a mock control. Remarkably, in all of these ALS models, high expression of Sema3A and NRP1 was measured.

Taken together, the combined in vivo and in vitro results suggest that the levels of both Sema3A and its co-binding receptor, NRP1, are pre-symptomatically increased in several ALS models as well as in sALS patients. These findings suggested that the Sema3A pathway is a common denominator in various ALS mutations, and thus it contributes to MN degeneration in ALS.

Example 2

Application of Sema3A on Wild-Type MN Axons Results in Axon Degeneration

Since the results herein above indicated that Sema3A is produced and secreted in excess from muscles of ALS models, and since muscles interact specifically with MN axons, the Sema3A activity was next tested in this distal subcellular compartment. To this end, a microfluidic chamber (MFC) that allows precise control, monitoring, and manipulation of subcellular microenvironments was utilized. Healthy ventral spinal cord (SC) explants from transgenic mouse embryos expressing GFP under the MN-specific promoter HB9 (HB9::GFP) were cultured in one compartment of the MFC and axons were enabled to extend into the opposing compartment, thus segregating axons and cell bodies into two isolated compartments. In order to verify that the MFCs can efficiently segregate MN axons from their somata, the neuronal culture in the MFC system were stained for the dendritic and axonal markers MAP2 and Tau, respectively. All neurites that traversed the distal compartment were confirmed to be positive for Tau staining and negative for MAP2.

Figure 2A:
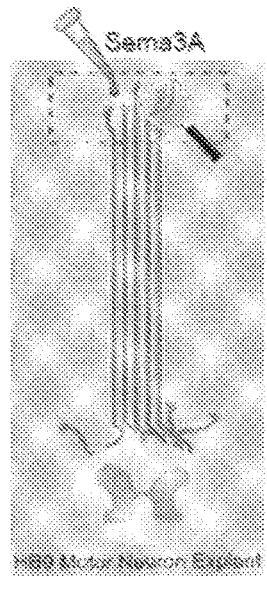
FIGS. 2A-F show that Sema3A as well as primary myocytes expressing diverse ALS-causing mutations impair the growth of wild-type HB9::GFP motor axons and enhance their retraction and degeneration.
Figure 2B:
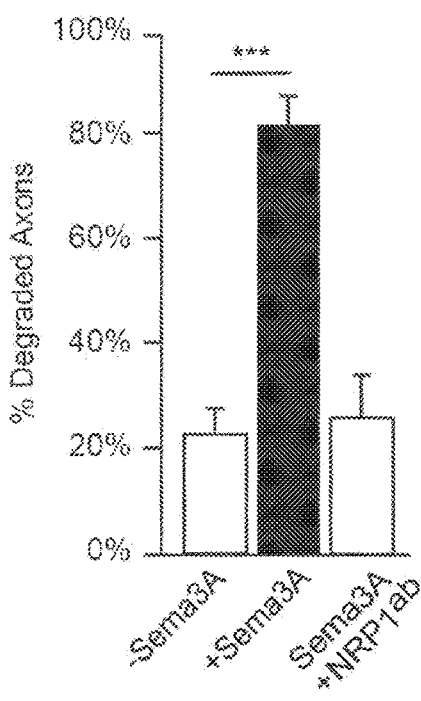

Next, Sema3A or control media were purified and applied to the distal compartment, while imaging the axons for 16 hours (FIG. 2A). The recordings revealed extensive axon degeneration in the Sema3A-treated MFCs 6-8 hours after its application. Co-application of NRP1-blocking antibody and Sema3A on MN axons inhibited the Sema3A-dependent axon degeneration (FIG. 2B).

Example 3

Muscles Expressing Diverse ALS Mutations Initiate Axon Degeneration

In order to study the molecular mechanisms enabling the communication between MNs and their environment, which are essential for cell survival and synapse maintenance, the MFC system was utilized to co-culture primary MNs and primary myocytes (Ionescu 2016, ibid). Ventral spinal cord (SC) explants from healthy 12-day-old (E12) HB9::GFP embryos were cultured in the proximal compartment, in the presence or absence of primary myocytes extracted from adult mice in the distal compartment. Culturing HB9::GFP explants in the presence of wild-type muscles was previously shown to facilitate the rapid and directed growth of axons into the distal compartment, suggesting that muscles secrete factors that support and promote the growth of motor axons. However, since previous studies indicated that ALS-mutated muscles have intrinsic abnormalities throughout disease progression, the possibility that the nature of these factors is altered was next examined.

Figure 2C:
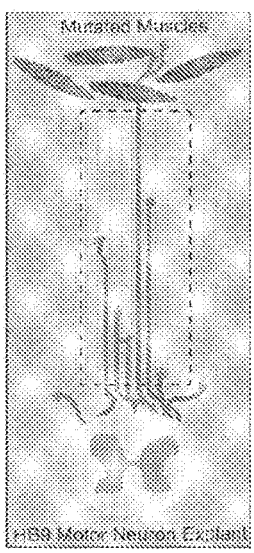
Figure 2D:
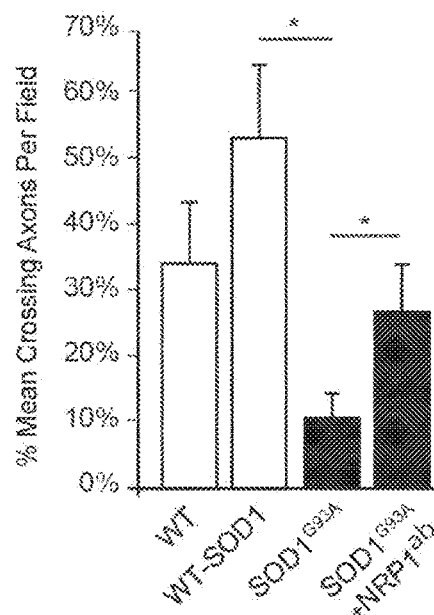

In order to study the effect of ALS muscles on MN axons in a simplified system, primary myocytes from pre-symptomatic P60 SOD1$^{G93A}$ and from LM mice as well as WT myocytes transfected to express SOD1$^{wt}$ were plated in the distal compartment. Myocyte cultures were allowed to fuse and differentiate. Importantly, in all the described cases myocyte morphology, fusion, and differentiation parameters were similar, and the culture showed no apparent difference. After 7 days, HB9::GFP Spinal Cord (SC) explants were cultured in the proximal compartment. Co-cultures were incubated until the HB9::GFP axons began extending toward the microgroove compartment. Once the axons reached the microgroove compartment, the extension of HB9::GFP axons along the microgrooves was recorded for 16 hours (FIG. 2C). Surprisingly, HB9::GFP axons that were co-cultured with the SOD1$^{G93A}$ myocytes were less likely to traverse the distal side (FIG. 2D). During this period, axons extending towards the SOD1$^{G93A}$ myocytes were markedly incapable of traversing the distal compartment and underwent retraction, degeneration, or remained static in place, as compared with the LM and SOD1$^{wt}$ controls. Noteworthy, the addition of NRP1-blocking antibodies to the distal compartment, targeting Sema3A binding to the extracellular site of NRP1, improved the traversing rate of axons (FIG. 2D).

Figure 2E:
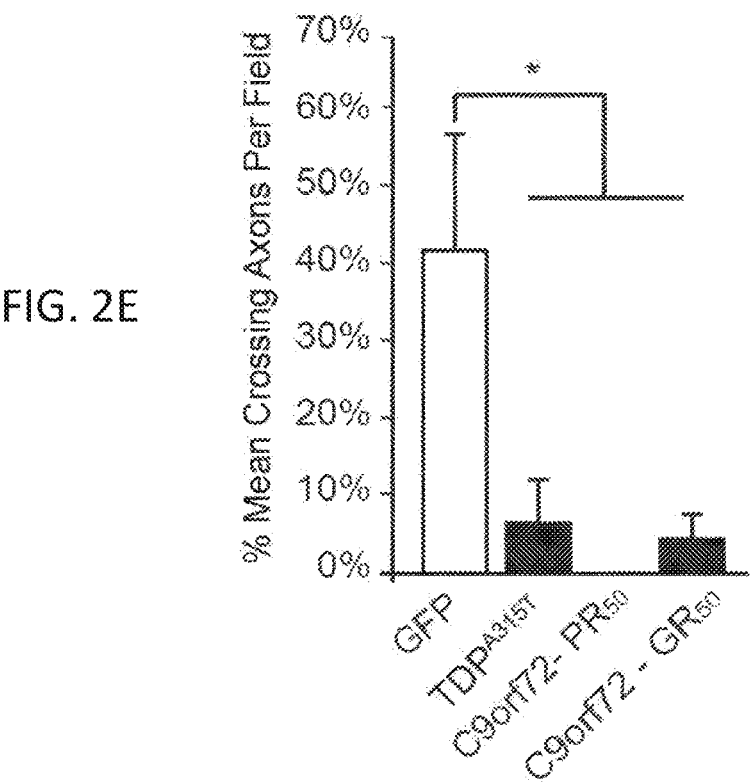

Primary myocyte cultures were further transfected with several more ALS-linked mutations or aberrant toxic proteins as follows: C9orf72-PR$_{50}$, C9orf72-GR$_{50}$, and TDP43$^{A315T}$ and used empty-GFP vector as a control. Transfected myocytes exhibited normal morphology and fusion in comparison with the WT muscle culture in this system. Nevertheless, all ALS-causing mutations that were examined recapitulated the phenotypes described previously in SOD1$^{G93A}$ (FIG. 2E). These results suggest that the dysregulated secretion of factors from ALS mutant muscles takes place, which in turn, activates axon retraction and degeneration.

Figure 2F:
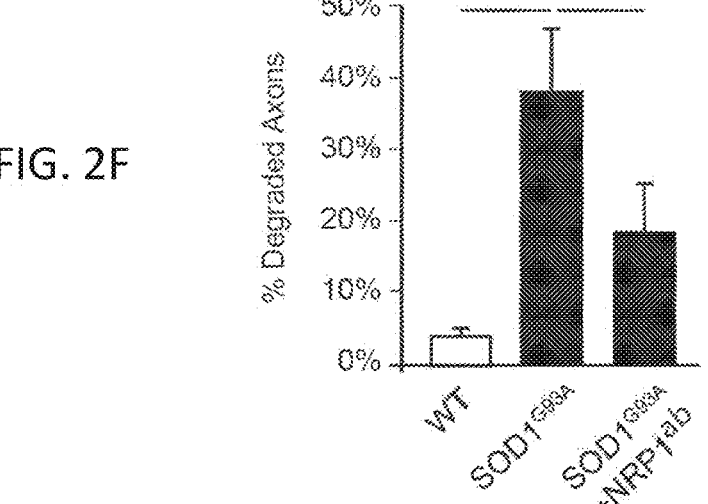

Because muscles can either secrete positive or negative signaling molecules, it was not clear whether the results presented herein above were due to an increase in the release of destabilizing factors or were due to the diminished release of positive factors. To this end, muscle-conditioned media was collected from WT and SOD1$^{G93A}$ muscle cultures in complete medium containing positive factors such as BDNF and GDNF and applied it only to the distal axons of both WT and SOD1$^{G93A}$ MNs (FIG. 2F). Interestingly, axon degeneration occurred only when SOD1$^{G93A}$ myocyte-conditioned media was applied to SOD1$^{G93A}$ axons (FIG. 2F), whereas in all other combinations the axons remained intact.

To further determine whether type 3 semaphorins such as Sema3A contribute to MN axon degeneration in this assay, the ability of NRP1-blocking antibody to block this phenotype was investigated. Here again, a rescue effect by this treatment was observed, although the protection was incomplete (FIG. 2F). These results indicated that ALS-mutated muscles secrete destabilizing factors such as Sema3A. Importantly, these results emphasized that SOD1$^{G93A}$ MNs exhibit a higher sensitivity to degeneration, and support the MN unique vulnerability as well as the non-cell autonomous mechanism of ALS. These results also indicated that Sema3A plays a complex role in MNs and that other related proteins are involved. Indeed, measuring other members of the Semaphorin family indicated that the percentage of NMJs expressing Sema3B as well as NRP2 was elevated in the SOD1$^{G93A}$ ALS model.

Thus, the destabilizing effect of ALS muscles over MN axons involves more than a single factor, and it cannot be blocked or rescued by targeting one factor at a time. Moreover, the multiplicity of effectors indicates that a higher-order regulator such as miRNA is involved in this process.

Figure 3A:
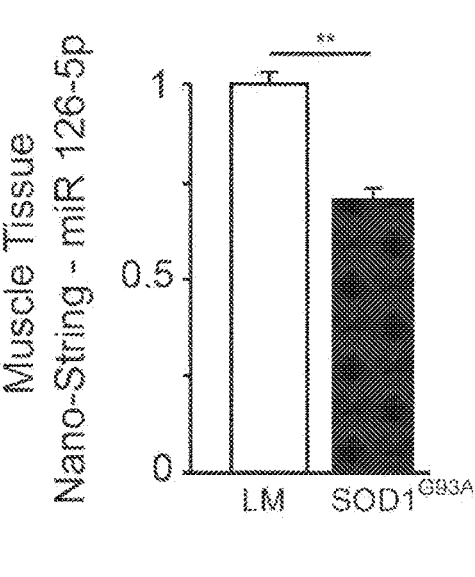
Figure 3B:
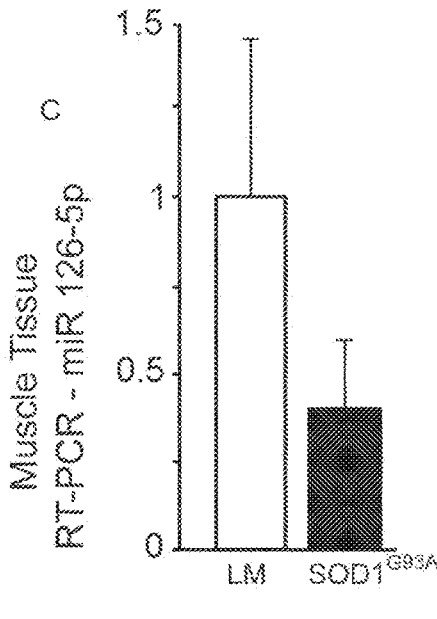
Figure 3C:
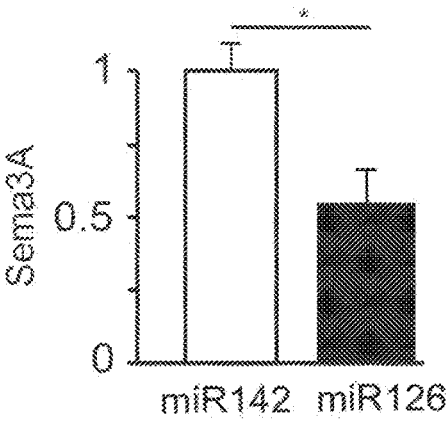
Figure 3D:
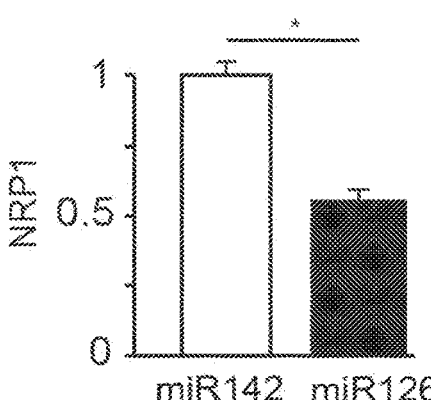

Example 4 miR126-5p is Down-Regulated in ALS Models and Modulates Sema3A, Sema3B, NRP1, and NRP2 Protein Expression Levels In order to identify the mechanism underlying the elevated levels of various secreted destabilizing factors in muscles of ALS models, alterations of miRNAs (miRs) which can regulate the expression of multiple proteins were evaluated. miRs have been previously linked to MN toxicity in ALS (Haramati et al., 2010). The screening for alterations was performed using Nanostring® miRNA-chip technology of ~800 miRs of pre-symptomatic P60 SOD1$^{G93A}$ mice and their LM controls. The screen yielded 8 significantly altered miRs. Since Sema3A levels were elevated in muscles, the focus narrowed to those miRs that were reduced and that could regulate its expression, specifically miR126-5p and miR133a (FIG. 3A).

qPCR was used to measure miR-126-5p levels in SOD1$^{G93A}$ GC muscles and the results indicated decreased levels of this miR (FIG. 3B). In order to verify that miR126-5p can regulate the expression of Semaphorin3 and Neuropilin signaling, HeLa cells, which are known to endogenously express Sema3A, Sema3B, NRP1, and NRP2, were transfected with miR126-5p or with the irrelevant miR142, which is not predicted to target any of these genes, as a negative control. To this end, RNA was isolated from these cultures and qPCR analysis was performed to determine the mRNA levels of Sema3A, Sema3B, NRP1, and NRP2. The results indicated that miR126-5p specifically targets Sema3A, NRP1, Sema3B, and NRP2 (FIGS. 3C-F).

To investigate whether miR126-5p overexpression can also inhibit Sema3A function, U87MG human glioblastoma cells, which express NRP1, were transfected to overexpress miR126-5p or miR142 as a control. One day after transfection, cells were re-suspended and plated in xCELLigence® multiwell electric plates. The next day, Sema3A was added to the cultures and any morphological or adhesive changes were monitored by the impedance readout. Adding Sema3A to responsive cells, such as U87MG cells, induced their detachment from the culture dish. This detachment was measured as a decrease in impedance. Shortly after Sema3A was added to the cultures, cells expressing miR142 exhibited decreased impedance, whereas cells expressing miR126-5p did not respond to Sema3A in the medium and kept growing with a corresponding increase in impedance (FIG. 3G).

Thus, these results indicate that the excess production of destabilizing factors in ALS is presumably mediated downstream of a deregulation in miR126-5p.

Example 5

Figures 4A, 4B, 4C:
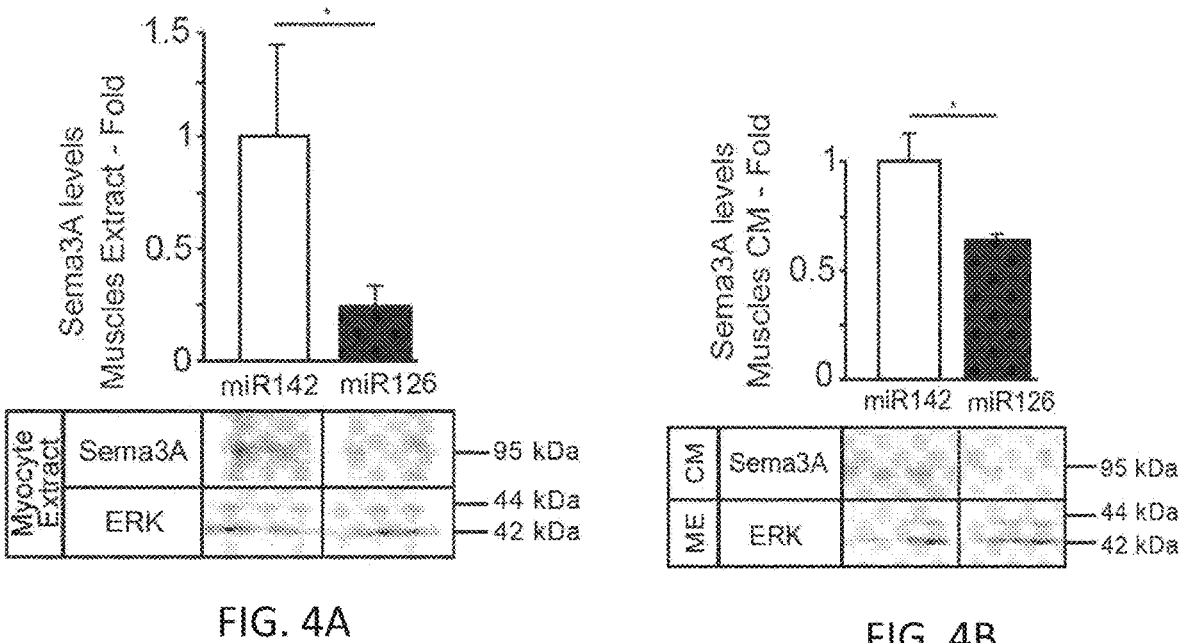

Overexpression of miR126-5p can Block SOD1$^{G93A}$ Muscle Toxicity In Vitro miR126-5p was overexpressed in SOD$^{G93A}$ myocyte cultures and the levels of Sema3 A in the cell extract as well as in the conditioned media were quantified. Western blot analysis indicated that Sema3A levels in both the cells extract and the conditioned media were depleted compared with miR142 (FIGS. 4A-B). Next, the question whether overexpression of miR126-5p in both SOD1$^{G93A}$ and PR$_{50}$ myocytes can rescue the negative effect on MN growth was investigated. To this end, primary myoblasts were transfected to overexpress either miR126-5p (SOD1$^{miR126}$; PR$_{50}$$^{miR126}$) or miR142 (SOD1$^{miR142}$; PR$_{50}$$^{miR142}$), and were then plated in the distal compartment of the MFC. Myoblasts were differentiated into mature myocytes while expressing the miRs for 7 days, after which HB9::GFP explants were cultured in the proximal compartment. Once axons reached the microgrooves, their extension toward the muscle compartment was monitored for 16 hours (FIG. 4C). Evidently, co-cultures with SOD1$^{miR126}$ and PR$_{50}$$^{miR126}$ myocytes retained wild-type behavior and manifested a clear rescue effect on the rate of axon traversal (FIGS. 4D-E).

Thus, myocytes expressing various ALS-linked mutations facilitate MN axon degeneration and delay their growth in a simplified compartmental co-culture assay. However, observing the co-cultures for longer periods showed that axons eventually do traverse the muscle compartment and form functional synapses with the myocytes. Using an image-based method to quantify contraction and assess the innervation in in vitro co-cultures (Ionescu 2016, ibid), contractile behavior of innervated SOD1$^{G93A}$ myocytes was found to be significantly different from that of innervated LM myocytes, which tend to contract in a bursting pattern (FIGS. 4F-G). Whereas 37% of innervated myocytes contracted in a bursting pattern, only 18% of the innervated SOD1$^{G93A}$ myocytes contracted in this pattern. Strikingly, SOD1$^{miR126}$ myocytes retained the same rate of bursting myocytes as the LM myocytes (FIG. 4G).

Taken together, these results indicate that miR126-5p is an effective regulator of muscle-secreted factors such as Sema3, and it rescues the detrimental effect of destabilizing factors on MN axons as well as on NMJ function and maintenance in vitro.

Example 6 miR126-5p Transiently Rescues Early Motor Phenotypes of SOD1$^{G93A}$ Mice In Vivo NMJ disruption, muscle morphology abnormalities, and Hind-limb misprints are major phenotypes in SOD1$^{G93A}$ mice. To determine whether miR126-5p can moderate those phenotypes, SOD1$^{G93A}$ mice were injected with either pLL-eGFP-miR126 (SOD1$^{miR126}$) or pLL-eGFP-miR142

Figure 5A:
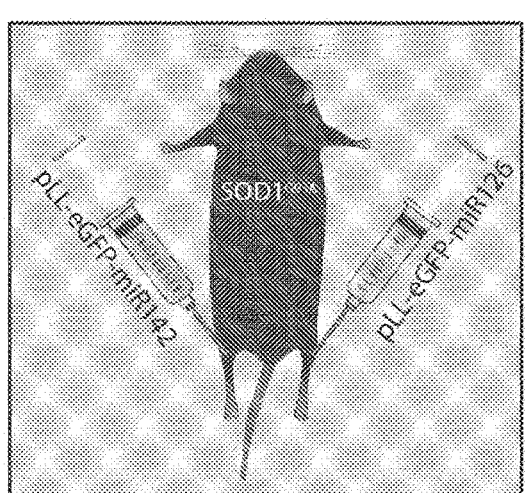
FIGS. 5A-G show pLL-eGFP-miR126-5p injected into GC muscles of pre-symptomatic SOD1$^{G93A}$ mice rescues the early phenotype appearance in vivo.

(SOD1$^{miR142}$) into the right and left GC muscles of pre-symptomatic mice (P60), respectively (FIG. 5A). Virus expression was validated both in vitro on MNs and in muscle cultures as well as in vivo at the transcript and protein levels. Importantly, the number of NMJs expressing Sema3A in the pLL-eGFP-miR126-5p-injected gastrocnemius muscles in comparison with the miR142 group was decreased, indicating that miR-126-5p is active in the injected tissue.

Figure 5B:
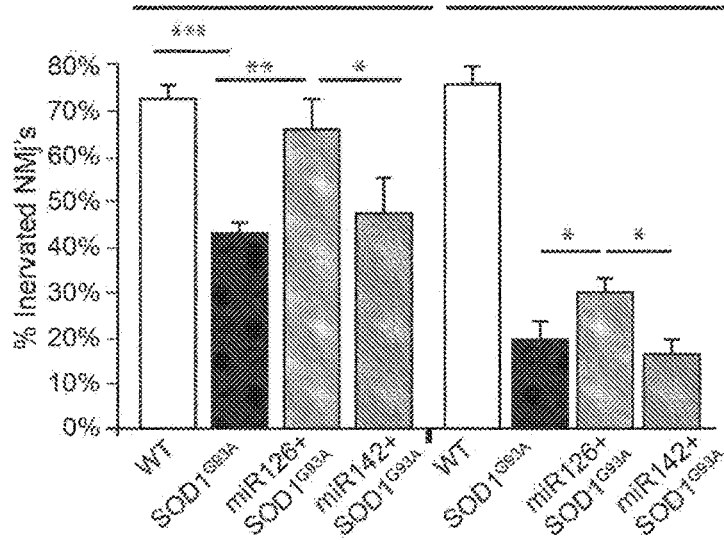

Next, a series of histological analyses, followed by motor behavioral tests at two time points post injection were performed: at the age at which mice typically begin exhibiting ALS phenotypes (P90) as well as in the disease end stage (P120). Since NMJ disruption is a key process in ALS, the effect of overexpression of miR126-5p on NMJ disruption was evaluated. Both the left and right GC muscles were fixed and stained for synaptic markers of the NMJ. Quantifying the percentage of intact NMJs at P90 injected mice revealed a significantly higher innervation rate in miR126-5p expressing muscles compared to both mock-treated and to SOD1$^{G93A}$ muscles (FIG. 5B). Furthermore, careful analysis at P120 also identified a mild rescue by miR-126-5p overexpression (FIG. 5B).

Figure 5C:
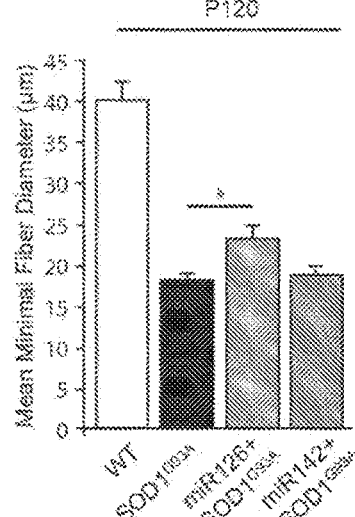

Next, histological analyses to determine muscle fiber wasting and tissue abnormalities were performed (FIG. 5C). P120 Gastrocnemius muscles of WT, SOD1$^{G93A}$, and both SOD1$^{miR126}$ and SOD1$^{miR142}$ were stained with H&E for histological examination and the minimal diameter of myofibers was analyzed. A significant increase in the minimal fiber size of the SOD1$^{miR126}$-injected muscle compared to the SOD1$^{miR142}$ mock control was observed (FIG. 5C).

Figure 5D:
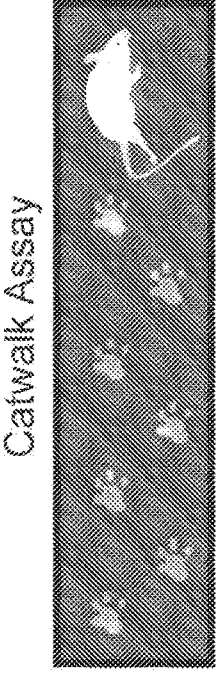
Figure 5E:
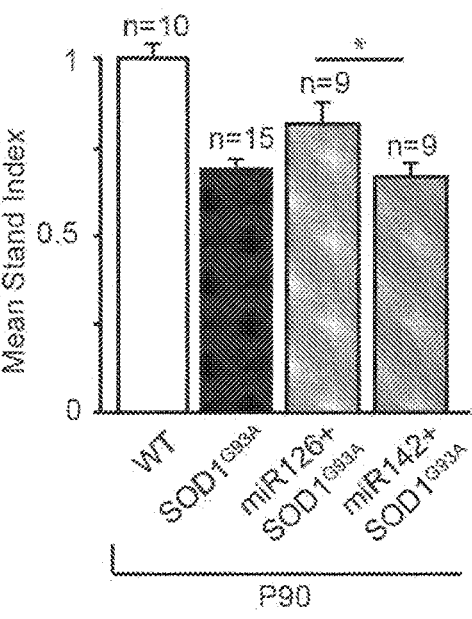
Figure 5F:
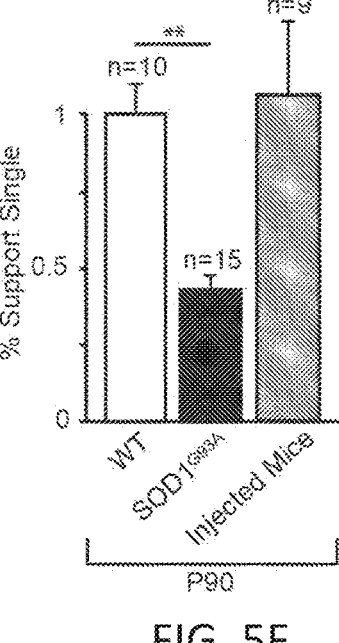
Figure 5G:
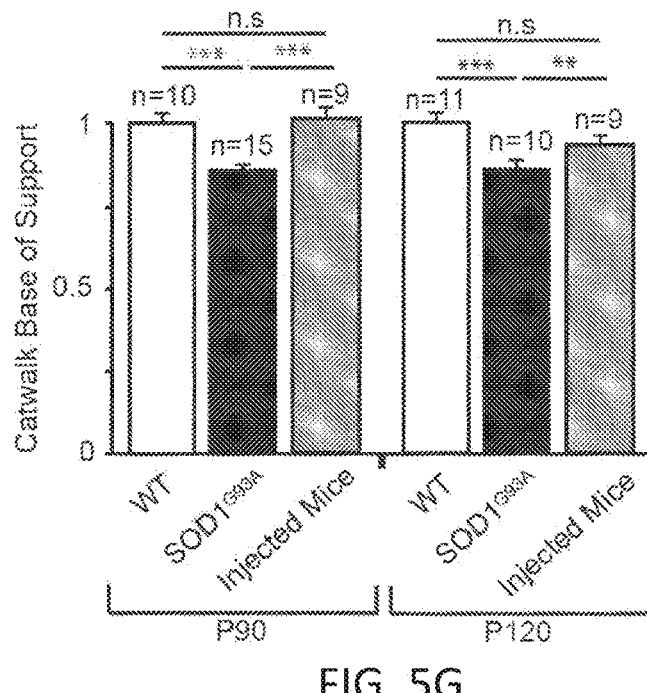

Lastly, a behavioral test using the CatWalk Gait Analysis technique was performed. This video-based method is a computerized version of the ink bath assay and provides an objective and dynamic wide range of gait analyses (FIG. 5D). One output is the Mean Stand Index (MSI), which measures the speed at which the paws detach from the walking surface. Since aged SOD1$^{G93A}$ mice suffer motor defects, their MSI values for both hind limbs are dramatically lower than their LM values. Remarkably, the MSI values of the SOD1$^{miR126}$-injected limbs were significantly higher at P90 and similar to the LM control values, whereas the SOD1$^{miR142}$-injected limb was reminiscent of typical SOD1$^{G93A}$ behavior (FIG. 5E). Other established parameters that have been shown to be altered in the SOD$^{G93A}$ model were examined: the percentage of single support parameter, which indicates the relative duration of contact of all combined paws with the glass floor, and the base of support parameter, which indicates the average width of limb spreading between both front and both hind paws. Remarkably, a significant rescue phenotype for both parameters in the injected mice at age of P90 was observed (FIG. 5F). Furthermore, the improvement in base of support parameter persisted also in P120 (FIG. 5G).

Taken together, these results indicate that miR126-5p reduces the detrimental effects of muscle-secreted destabilizing factors such as Sema3A on MN axons and motor function in ALS models in vivo.

Figure 6:
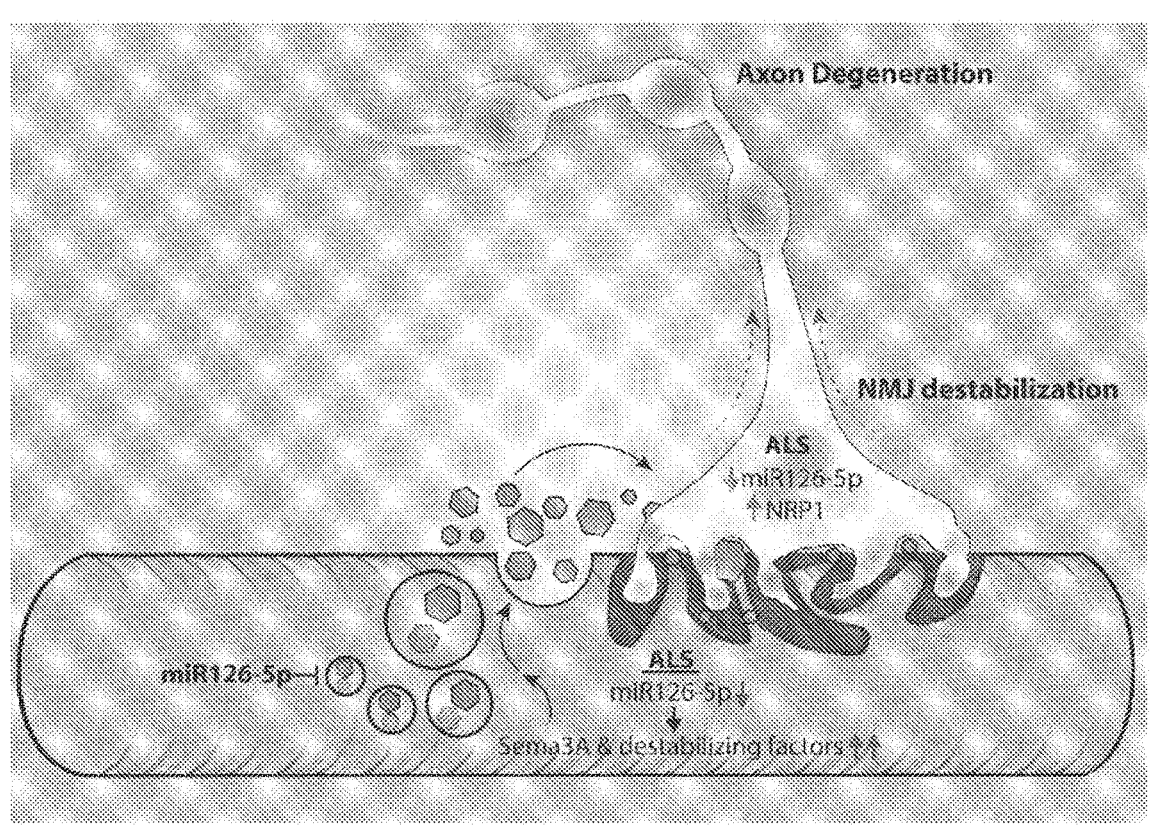
FIG. 6 shows that alterations in Semaphorin3A regulation by miR126-5p trigger motor neuron degeneration in ALS; miR126-5p is a negative regulator of Sema3 signaling in skeletal muscles. Down-regulation of miR126-5p in ALS disease drives the overexpression and secretion of Sema3A and potentially other NMJ destabilizing factors in skeletal muscles. The down-regulation in miR126-5p in diseased MNs drives the overexpression of NRP1 specifically in axons. The excess binding and activation of the NRP1 receptor by its overexpressed ligand Sema3A as a result of miR126-5p alteration promotes NMJ disruption and axon degeneration in a spatially confined process.

FIG. 6 depicts the interplay between Sema3A and miR126-5p in ALS muscles and motor neurons and their effects on NMJ disruption and axon degeneration.

Example 7

Therapeutic Efficacy of miR126-5p Overexpression in Muscles and miR126-5p Silencing in Spinal Cord in ALS Mouse Models The aim of this study is to evaluate the effect of miR126-5p overexpression in skeletal muscles and miR126-5p knockdown in the CNS by an antisense of miR126-5p on axonal degeneration in ALS mouse models. The effects of miR126-5p overexpression in skeletal muscles and silencing of miR126-5p in glial cells of spinal cord on ALS pathology are evaluated by both histological and behavioural tests. Two lentiviral vectors are used: one vector containing glial cell specific promoter with miR126-5p antisense (pLKO$^{miR126}$) and another vector containing muscle specific promoter with miR126-5p (pLL$^{mir126}$). The lentiviral vector pLKO$^{miR126}$ under glial fibrillary acidic protein (GFAP) promoter (astrocytes specific) is used to efficiently reduce miR126-5p levels in spinal cord glial cells. The pLKO$^{miR126}$ (or scrambled control) is tested after disease onset. Delivery is done by intrathecal injections. A total of 3×10$^9$ particles of pLKO$^{miR126}$ in a total volume of 3 μl are injected slowly into the CSF through a 33-gauge needle and a Hamilton syringe between lumbar vertebrae L3 and L4. Access to the intrathecal space is confirmed by the animal's tail movement.

The lentiviral vector pLL$^{miR126}$ under the α-skeletal actin promoter is used to overexpress miR126-5p levels in the muscles. Delivery is done by either subcutaneous or intramuscular injections bilaterally into large muscle bundles by injecting a total of 1×10$^6$ titer units (tu) in 25 μl of PBS. This delivery method addresses the peripheral role of miR126-5p at the neuromuscular junction and axons. miR126-5p levels are evaluated as well as their histopathological impact on motor neurons, NMJ, muscle and spinal cord. Several behavioural motor tests using the catwalk device and survival assays are also performed.

Example 8

Effect of miR126-5p Overexpression in Spinal Cord Motor Neurons

Figure 7A:
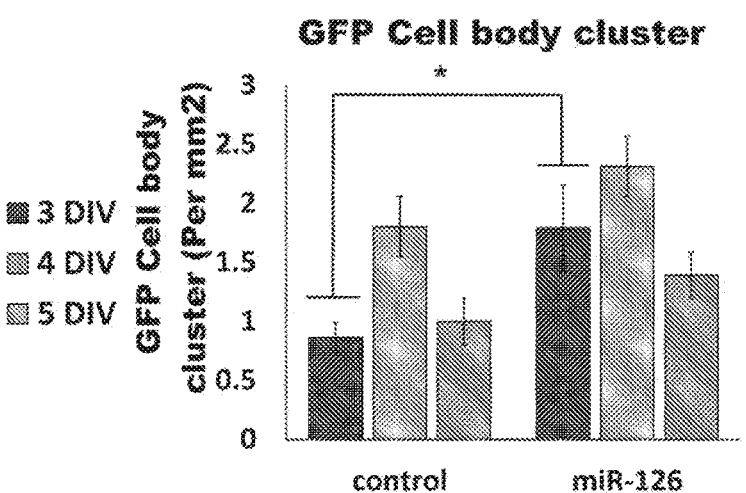
FIGS. 7A-B show that overexpression of miR126-5p in motor neuron culture enhance cell viability and axon growth. Wild type E12.5 primary spinal cord neurons were infected with either miR126-5p or miR142 as a control 2 hours after plating. Neurite length (FIG. 7A) and cell body cluster (FIG. 7B) were measured using the incuCyte imaging system after 3, 4 and 5 days in vitro (DIV).
Figure 7B:
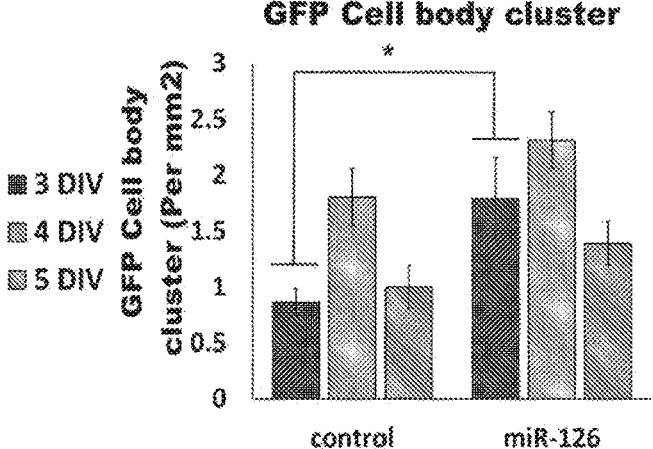

The effect of miR126-5p overexpression in spinal cord motor neurons was next examined. Primary spinal cord motor neurons were infected two hours after plating with lentivirus expressing either miR126-5p or miR142 (control). Neurite length and cell body clusters were measured using incuCyte imaging system after 3, 4 and 5 days in vitro (DIV). FIG. 7A shows neurite length quantification and the results indicated a significant increase in neurite length in the miR126-5p transfected group in comparison to its control at 3, 4 and 5 DIV (3 biological repeats, Student t test; * p<0.05). FIG. 7B shows cell body cluster quantification and the results indicated a significant increase in cell body cluster in the miR126-5p transfected group in comparison to its control at 3 DIV (3 biological repeats, Student t test; p<0.05). These results show that miR126-5p overexpression in spinal cord motor neurons has a beneficial effect on axon length and neuron survival.

Example 9

Effect of miR126-5p Overexpression in Spinal Cord Motor Neurons of ALS Mice

Figure 8A:
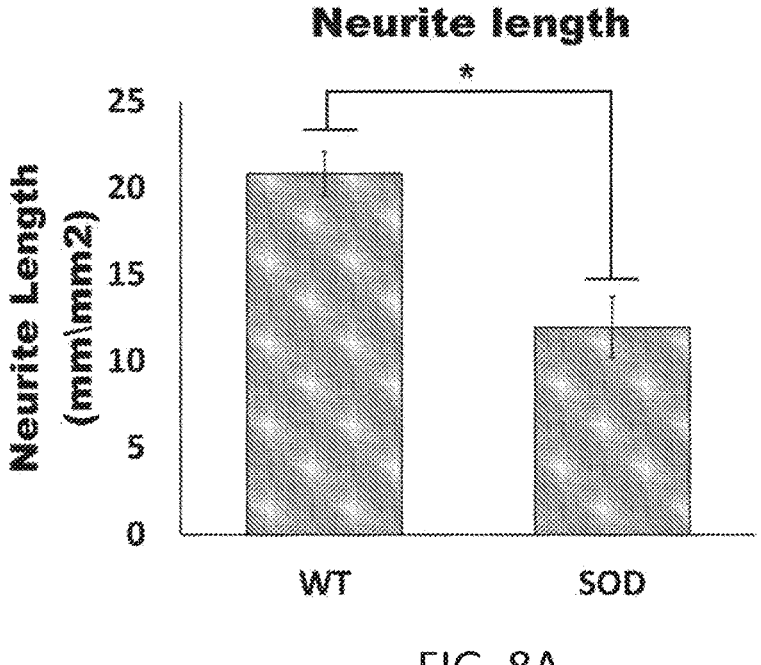
FIGS. 8A-B show that overexpression of miR126-5p in SOD$^{G93A}$ motor neuron cultures has positive effect on neurite growth. E12.5 primary SC neuron cultures of either WT, SOD$^{G93A}$ or SOD$^{G93A}$ overexpressing miR126-5p were evaluated for neurite length using the incuCyte imaging system after 3 DIV.
Figure 8B:
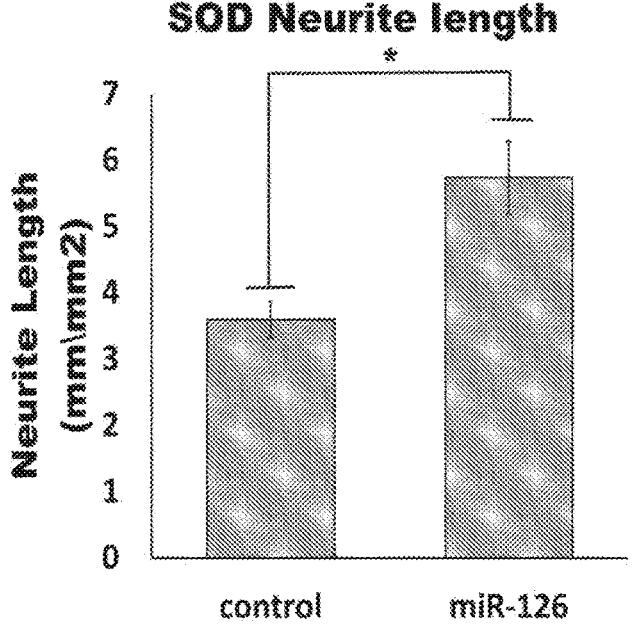

The effect of miR126-5p overexpression in motor neurons of ALS mice was next examined. Primary spinal cord motor neuron cultures from wild-type (WT), from the ALS mice model SOD$^{G93A}$, or from the ALS mice model SOD$^{G93A}$ overexpressing miR126-5p were evaluated for neurite length. As shown in FIG. 8A, spinal cord motor neurons of $SOD^{G93A}$ grew shorter axons as compared to motor neurons of the WT group. Overexpression of miR126-5p in the $SOD^{G93A}$ motor neuron cultures resulted in enhanced neurite growth (FIG. 8B). These results indicated that overexpression of miR126-5p in motor neurons of ALS mice model induces axon growth, thereby having a rescue effect.

REFERENCES

1. Di Pietro L, Baranzini M, Berardinelli M G, Lattanzi W, Monforte M, Tasca G, Conte A, Logroscino G, Michetti F, Ricci E, Sabatelli M, Bernardini C (2017) Potential therapeutic targets for ALS: MIR206, MIR208b and MIR499 are modulated during disease progression in the skeletal muscle of patients. Sci Rep 7:9538.
2. Emde A, Hornstein E (2014) miRNAs at the interface of cellular stress and disease. EMBO J 33:1428-1437.
3. Haramati S, Chapnik E, Sztainberg Y, Eilam R, Zwang R, Gershoni N, McGlinn E, Heiser P W, Wills A-M, Wirguin I, Rubin L L, Misawa H, Tabin C J, Brown R, Chen A, Hornstein E (2010) miRNA malfunction causes spinal motor neuron disease. Proc Natl Acad Sci USA 107: 13111-13116.
4. Hawley Z C E, Campos-*Melo* D, Droppelmann C A, Strong M J (2017) MotomiRs: miRNAs in Motor Neuron Function and Disease. Front Mol Neurosci 10:127.
5. Ionescu A, Zahavi E E, Gradus T, Ben-Yaakov K, Perlson E (2016) Compartmental microfluidic system for studying muscle-neuron communication and neuromuscular junction maintenance. Eur J Cell Biol 95:69-88.
6. Lemmens R, Moore M J, Al-Chalabi A, Brown R H, Robberecht W (2010) RNA metabolism and the pathogenesis of motor neuron diseases. Trends Neurosci 33:249-258.
7. Maimon R, Ionescu A, Bonnie A, Sweetat S, Wald-Altman S, Gradus T, Weil M, Behar O, Trotti D, Perlson E (2017) Muscle secretion of toxic factors regulated by miR126-5P facilitate motor neuron degeneration in ALS. J. Neurol. Sci. abstract no. 2264; doi: 10.1016/j.jns.2017.08.2295.
8. Maimon R, Ionescu A, Bonnie A, Sweetat S, Wald-Altman S, Inbar S, Gradus T, Trotti D, Weil M, Behar O,
9. Perlson E (2018) miRNA126-5p downregulation facilitates axon degeneration and NMJ disruption via a non-cell-autonomous mechanism in ALS. J. Neuroscience 38 (24): 5478-5494.
9. Maimon R and Perlson E (2019) Neural Regen Res IP: 77.139.239.91.
10. Molasy M, Walczak A, Szaflik J, Szaflik J P, Majsterek I (2017) MicroRNAs in glaucoma and neurodegenerative diseases. J Hum Genet 62:105-112.
11. Molofsky A V, Kelley K W, Tsai H-H, Redmond S A, Chang S M, Madireddy L, Chan J R, Baranzini S E, Ullian E M, Rowitch D H (2014) Astrocyte-encoded positional cues maintain sensorimotor circuit integrity. Nature 509: 189-194.
12. Nachmany H, Wald S, Abekasis M, Bulvik S, Weil M (2012) Two potential biomarkers identified in mesenchymal stem cells and leukocytes of patients with sporadic amyotrophic lateral sclerosis. Dis Markers 32:211-220.
13. Rotem N, Magen I, Ionescu A, Gershoni-Emek N, Altman T, Costa C J, Gradus T, Pasmanik-Chor M, Willis D E, Ben-Dov I Z, Hornstein E, Perlson E (2017) ALS Along the Axons-Expression of Coding and Noncoding RNA Differs in Axons of ALS models. Sci Rep 7:44500.
14. Wen X, Tan W, Westergard T, Krishnamurthy K, Markandaiah S S, Shi Y, Lin S, Shneider N A, Monaghan J, Pandey U B, Pasinelli P, Ichida J K, Trotti D (2014) Antisense proline-arginine RAN dipeptides linked to C9ORF72-ALS/FTD form toxic nuclear aggregates that initiate in vitro and in vivo neuronal death. Neuron 84:1213-1225.

The work leading to this invention has received funding from the European Research Council under the European Union's Seventh Framework Program (FP7/2007-2013)/ERC grant agreement n° 309377.

It is appreciated by persons skilled in the art that the present invention is not limited by what has been particularly shown and described hereinabove. Rather the scope of the present invention includes both combinations and subcombinations of various features described hereinabove as well as variations and modifications. Therefore, the invention is not to be constructed as restricted to the particularly described embodiments, and the scope and concept of the invention will be more readily understood by references to the claims, which follow.

---

The invention claimed is:

1. A method for treating a motor neuron disease (MND), the method comprising administering to a subject in need of such treatment a therapeutically effective amount of a pharmaceutical combination comprising:

(a) a first pharmaceutical composition comprising a therapeutically effective amount of an agent selected from the group consisting of: (i) microRNA (miR) 126-5p, a precursor, or a homolog thereof; (ii) a polynucleotide encoding miR126-5p, a precursor or a homolog thereof; and (iii) an expression vector comprising a polynucleotide encoding miR126-5p, a precursor or a homolog thereof, wherein the polynucleotide and the expression vector comprising the polynucleotide further comprises a muscle specific promoter, and wherein the first pharmaceutical composition is effective to increase miR126-5p expression in a skeletal muscle cell; and (b) a second pharmaceutical composition comprising a therapeutically effective amount of an agent selected from the group consisting of: (i) miR126-5p, a precursor or a homolog thereof; (ii) a polynucleotide encoding miR126-5p, a precursor or a homolog thereof; and (iii) an expression vector comprising a polynucleotide encoding miR126-5p, a precursor or a homolog thereof, wherein the polynucleotide and the expression vector comprising the polynucleotide further comprises a neuron specific promoter, and wherein the second pharmaceutical composition is effective to increase miR126-5p expression in a motor neuron;

wherein the MND is selected from the group consisting of Amyotrophic Lateral Sclerosis (ALS), primary lateral sclerosis, progressive muscular atrophy, pseudobulbar palsy and progressive bulbar palsy;

wherein the miR126-5p consists of the nucleotide sequence set forth in SEQ ID NO: 1, and wherein a homolog thereof comprises a seed region identical to positions 2-8 of SEQ ID NO: 1, and is at least 90% identical to SEQ ID NO: 1.

2. The method according to claim 1, wherein the pharmaceutical compositions are administered simultaneously or sequentially.

3. The method according to claim 1, wherein the pharmaceutical combination comprises the following pharmaceutical compositions: (a) a first pharmaceutical composition comprising a therapeutically effective amount of the expression vector comprising a polynucleotide encoding miR126-5p, a precursor or a homolog thereof, wherein the first pharmaceutical composition is effective to increase miR126-5p expression in a skeletal muscle cell; and (b) a second pharmaceutical composition comprising a therapeutically effective amount of the expression vector comprising a polynucleotide encoding miR126-5p, a precursor or a homolog thereof, wherein the second pharmaceutical composition is effective to increase miR126-5p expression in a motor neuron.

4. The method according to claim 1, wherein at least one of the expression vectors is a viral vector.

5. The method according to claim 4, wherein the viral vector is selected from the group consisting of lentiviral vectors and adeno-associated viral vectors.

6. The method according to claim 5, wherein the lentiviral vector is selected from the group consisting of an HIV-based lentiviral vector, an EIAV-based lentiviral vector, and self-inactivating (SIN) lentiviral vector.

7. The method according to claim 1, wherein the muscle specific promoter is a skeletal muscle specific promoter.

8. The method according to claim 1, wherein the muscle specific promoter is selected from the group consisting of skeletal muscle α-actin promoter, myogenin promoter, and muscle creatine kinase promoter.

9. The method according to claim 1, wherein the neuron specific promoter is selected from the group consisting of neurofilament promoter, HB9 promoter, Thy-1 promoter, and synapsin promoter.

10. The method according to claim 1, wherein the muscle specific promoter is a skeletal muscle α-actin promoter, and wherein the neuron specific promoter is a neurofilament promoter.

11. The method according to claim 1, wherein the first pharmaceutical composition is formulated for intramuscular, intravenous, or intra-arterial injection.

12. The method according to claim 1, wherein the second pharmaceutical composition is formulated for injection or infusion into the spinal cord or CNS.

13. The method according to claim 1, wherein the pharmaceutical combination comprises:

(a) the first pharmaceutical composition comprising an expression vector comprising SEQ ID NO: 1 operably linked to a skeletal muscle α-actin promoter, and wherein the first pharmaceutical composition is formulated for injection into a skeletal muscle tissue; and (b) the second pharmaceutical composition comprising an expression vector comprising SEQ ID NO: 1 operably linked to a neurofilament promoter, and wherein the second pharmaceutical composition is formulated for injection or infusion into the spinal cord or CNS.

14. A method of treating a motor neuron disease (MND), the method comprising administering to a subject having the MND at least one pharmaceutical composition selected from:

a first pharmaceutical composition comprising an agent selected from the group consisting of: (i) miR126-5p, a precursor or a homolog thereof; (ii) a polynucleotide encoding miR126-5p, a precursor or a homolog thereof; and (iii) an expression vector comprising a polynucleotide encoding miR126-5p, a precursor or a homolog thereof, wherein the polynucleotide and the expression vector comprising the polynucleotide further comprises a muscle specific promoter, and wherein the first pharmaceutical composition is effective to increase miR126-5p expression in a skeletal muscle cell; and a second pharmaceutical composition comprising an agent selected from the group consisting of: (i)

miR126-5p, a precursor or a homolog thereof; (ii) a polynucleotide encoding miR126-5p, a precursor or a homolog thereof; and (iii) an expression vector comprising a polynucleotide encoding miR126-5p, a precursor or a homolog thereof, wherein the polynucleotide and the expression vector comprising the polynucleotide further comprises a neuron specific promoter, and wherein the second pharmaceutical composition is effective to increase miR126-5p expression in a motor neuron; and wherein the MND is selected from the group consisting of Amyotrophic Lateral Sclerosis (ALS), primary lateral sclerosis, progressive muscular atrophy, pseudobulbar palsy and progressive bulbar palsy; wherein the miR126-5p consists of the nucleotide sequence set forth in SEQ ID NO: 1, and wherein a homolog thereof comprises a seed region identical to positions 2-8 of SEQ ID NO: 1, and is at least 90% identical to SEQ ID NO: 1.

* * * * *

SEQUENCE LISTING

<160> NUMBER OF SEQ ID NOS: 22

<210> SEQ ID NO 1
<211> LENGTH: 21
<212> TYPE: RNA
<213> ORGANISM: Artificial sequence
<220> FEATURE:
<223> OTHER INFORMATION: Synthetic sequence

<400> SEQUENCE: 1
cauuauuacu uuugguacgc g                                              21

<210> SEQ ID NO 2
<211> LENGTH: 85
<212> TYPE: RNA
<213> ORGANISM: Artificial sequence
<220> FEATURE:
<223> OTHER INFORMATION: Synthetic sequence

<400> SEQUENCE: 2
cgcuggcgac gggacauuau uacuuuuggu acgcgcugug acacuucaaa cucguaccgu          60
gaguaauaau gcgccgucca cggca                                               85

<210> SEQ ID NO 3
<211> LENGTH: 22
<212> TYPE: RNA
<213> ORGANISM: Artificial sequence
<220> FEATURE:
<223> OTHER INFORMATION: Synthetic sequence

<400> SEQUENCE: 3
ucguaccgug aguaauaaug cg                                                   22

<210> SEQ ID NO 4
<211> LENGTH: 21
<212> TYPE: DNA
<213> ORGANISM: Artificial sequence
<220> FEATURE:
<223> OTHER INFORMATION: Synthetic sequence

<400> SEQUENCE: 4
gtaataatga aaccatgcg c                                                     21

<210> SEQ ID NO 5
<211> LENGTH: 25
<212> TYPE: DNA
<213> ORGANISM: Artificial sequence
<220> FEATURE:
<223> OTHER INFORMATION: Synthetic sequence

<400> SEQUENCE: 5
gaaccaggtt atgaccttga tttat                                               25

<210> SEQ ID NO 6
<211> LENGTH: 19
<212> TYPE: DNA
<213> ORGANISM: Artificial sequence
<220> FEATURE:
<223> OTHER INFORMATION: Synthetic sequence

<400> SEQUENCE: 6
gcaagacgtt cagtcctgt                                                       19

<210> SEQ ID NO 7
<211> LENGTH: 26
<212> TYPE: DNA
<213> ORGANISM: Artificial sequence
<220> FEATURE:
<223> OTHER INFORMATION: SYnthetic sequence

<400> SEQUENCE: 7
gctccagtta tcataccttc cttttg                                              26

<210> SEQ ID NO 8
<211> LENGTH: 22
<212> TYPE: DNA
<213> ORGANISM: Artificial sequence
<220> FEATURE:
<223> OTHER INFORMATION: Synthetic sequence

<400> SEQUENCE: 8
actggccaca caatcttttg aa                                                   22

<210> SEQ ID NO 9

-continued

```
<211> LENGTH: 20
<212> TYPE: DNA
<213> ORGANISM: Artificial sequence
<220> FEATURE:
<223> OTHER INFORMATION: Synthetic sequence

<400> SEQUENCE: 9
acctgttctc tttcagggaa                                                    20

<210> SEQ ID NO 10
<211> LENGTH: 20
<212> TYPE: DNA
<213> ORGANISM: Artificial sequence
<220> FEATURE:
<223> OTHER INFORMATION: Synthetic sequence

<400> SEQUENCE: 10
caagttgcag gcttgattcg                                                    20

<210> SEQ ID NO 11
<211> LENGTH: 20
<212> TYPE: DNA
<213> ORGANISM: Artificial sequence
<220> FEATURE:
<223> OTHER INFORMATION: Synthetic sequence

<400> SEQUENCE: 11
ccgtgtgaac catgtgactt                                                    20

<210> SEQ ID NO 12
<211> LENGTH: 21
<212> TYPE: DNA
<213> ORGANISM: Artificial sequence
<220> FEATURE:
<223> OTHER INFORMATION: Synthetic sequence

<400> SEQUENCE: 12
ggcatcttca aacctccatg a                                                  21

<210> SEQ ID NO 13
<211> LENGTH: 17
<212> TYPE: DNA
<213> ORGANISM: Artificial sequence
<220> FEATURE:
<223> OTHER INFORMATION: Synthetic sequence

<400> SEQUENCE: 13
gaggccaacc agaccca                                                       17

<210> SEQ ID NO 14
<211> LENGTH: 22
<212> TYPE: DNA
<213> ORGANISM: Artificial sequence
<220> FEATURE:
<223> OTHER INFORMATION: Synthetic sequence

<400> SEQUENCE: 14
cgtaaacaat ccactcgcag tt                                                 22

<210> SEQ ID NO 15
<211> LENGTH: 16
<212> TYPE: DNA
<213> ORGANISM: Artificial sequence
<220> FEATURE:
<223> OTHER INFORMATION: Synthetic sequence

<400> SEQUENCE: 15
```

```
tctccttcca agtcca                                                        16

<210> SEQ ID NO 16
<211> LENGTH: 17
<212> TYPE: DNA
<213> ORGANISM: Artificial sequence
<220> FEATURE:
<223> OTHER INFORMATION: Synthetic sequence

<400> SEQUENCE: 16
ctcggcaccc acaaaca                                                       17

<210> SEQ ID NO 17
<211> LENGTH: 19
<212> TYPE: DNA
<213> ORGANISM: Artificial sequence
<220> FEATURE:
<223> OTHER INFORMATION: Synthetic sequence

<400> SEQUENCE: 17
cactgggatt gcctgtctt                                                     19

<210> SEQ ID NO 18
<211> LENGTH: 20
<212> TYPE: DNA
<213> ORGANISM: Artificial sequence
<220> FEATURE:
<223> OTHER INFORMATION: Synthetic sequence

<400> SEQUENCE: 18
ggccaagcca ttaaaagtga                                                    20

<210> SEQ ID NO 19
<211> LENGTH: 22
<212> TYPE: DNA
<213> ORGANISM: Artificial sequence
<220> FEATURE:
<223> OTHER INFORMATION: Synthetic sequence

<400> SEQUENCE: 19
gctaccccga ccacatgaag ca                                                 22

<210> SEQ ID NO 20
<211> LENGTH: 24
<212> TYPE: DNA
<213> ORGANISM: Artificial sequence
<220> FEATURE:
<223> OTHER INFORMATION: Synthetic sequence

<400> SEQUENCE: 20
gtcttgtagg tgccgtcgtc cttg                                               24

<210> SEQ ID NO 21
<211> LENGTH: 20
<212> TYPE: DNA
<213> ORGANISM: Artificial sequence
<220> FEATURE:
<223> OTHER INFORMATION: Synthetic sequence

<400> SEQUENCE: 21
gtgtggctgt taggcatggt                                                    20

<210> SEQ ID NO 22
<211> LENGTH: 20
<212> TYPE: DNA
```

-continued

```
<213> ORGANISM: Artificial sequence
<220> FEATURE:
<223> OTHER INFORMATION: Synthetic sequence

<400> SEQUENCE: 22
cattgcactg tccactcctg                                                    20
```